(12) United States Patent
Strongin et al.

(10) Patent No.: US 8,350,064 B2
(45) Date of Patent: Jan. 8, 2013

(54) FLUORESCENT XANTHENES AND WHITE LIGHT FLUOROPHORES

(75) Inventors: Robert M. Strongin, Portland, OR (US); Isiah M. Warner, Baton Rouge, LA (US); Youjun Yang, Austin, TX (US); Mark Lowry, Baton Rouge, LA (US); Sayo O. Fakayode, Winston-Salem, NC (US); Jorge O. Escobedo Cordova, Portland, OR (US); Xiangyang Xu, Columbia, MO (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 687 days.

(21) Appl. No.: 12/374,111

(22) PCT Filed: Jul. 19, 2007

(86) PCT No.: PCT/US2007/073864
§ 371 (c)(1),
(2), (4) Date: Sep. 21, 2009

(87) PCT Pub. No.: WO2008/011508
PCT Pub. Date: Jan. 24, 2008

(65) Prior Publication Data
US 2010/0051826 A1    Mar. 4, 2010

Related U.S. Application Data

(60) Provisional application No. 60/832,413, filed on Jul. 21, 2006.

(51) Int. Cl.
*C07D 311/78* (2006.01)
(52) U.S. Cl. .......................................... 549/384; 424/9.6
(58) Field of Classification Search .................. 549/384; 424/9.6
See application file for complete search history.

(56) References Cited

U.S. PATENT DOCUMENTS

| | | | |
|---|---|---|---|
| 4,710,570 A | 12/1987 | Thien | 549/31 |
| 4,945,171 A | 7/1990 | Haugland et al. | 549/224 |
| 5,624,847 A | 4/1997 | Lakowicz et al. | 436/68 |
| 5,903,340 A | 5/1999 | Lawandy et al. | 356/71 |
| 5,922,612 A | 7/1999 | Alder et al. | 436/163 |
| 6,008,379 A | 12/1999 | Benson et al. | 549/224 |
| 6,023,371 A | 2/2000 | Onitsuka et al. | 359/620 |
| 6,372,907 B1 | 4/2002 | Lee et al. | 546/41 |
| 7,038,063 B2 | 5/2006 | Lee et al. | 549/224 |
| 2004/0242902 A1 | 12/2004 | Lam et al. | 549/225 |
| 2005/0279247 A1 | 12/2005 | Auslander et al. | 106/31.28 |

OTHER PUBLICATIONS

Bowers, M. et al., "White-Light Emission from Magic-Sized Cadmium Selenide Nanocrystais," J. Am. Chem. Soc. vol. 127, pp. 15378-15379 (2005).

Chang, C. et al., "A tautomeric zinc sensor for ratiometric fluorescence imaging: Application to nitric oxide-induced release of intracellular zinc," *Proc. Natl. Acad. USA*, vol. 101, pp. 1129-1134 (2004).
Fabian, W. et al., "Effects of annulation on absorption and fluorescence characteristics of fluorescein derivatives: a computational study," *J. Chem. Soc, Perkin Trans.*, vol. 2, No. 5, pp. 853-856 (1996).
Furuta, P. et al., *J. Am. Chem. Soc.*, vol. 126, pp. 15388-15389 (2004).
Han et al., "Quantum-dot-tagged microbeads for multiplexed optical coding of biomolecules," Nature Biotechnology, vol. 19, pp. 631-635 (2001).
Hutchison, K. et al., "Bucky Light Bulbs: White Light Electroluminescence from a Fluorescent $C_{60}$, Adduct-Single Layer Organic LED," *J. Am. Chem. Soc.*, vol. 121, pp. 5611-5612 (1999).
Jia, W. et al., "$Mes_2B(p$-4,4'-biphenyl-NPh(1-naphthyl)): A Multifunctional Molecule for Electroluminescent Devices," *Chem. Mater.*, vol. 17, pp. 164-170 (2005).
Lee, L. et al., "Vita Blue: A New 633-nm Excitable Fluorescent Dye for Cell Analysis," *Cytometry*, vol. 10, pp. 151-164 (1989).
Liao, Y., "Direct White Light Phosphor: A Porous Zinc Gallophosphate with Tunable Yellow-to-White Luminescence," *J. Am. Chem. Soc.*, vol. 127, pp. 9986-9987 (2005).
Liu, Y. et al., "π-Conjugated Aromatic Enzynes as a Single-Emitting Component for White Electroluminescence," *J. Am. Chem. Soc.*, vol. 128, pp. 5592-5593 (2006).
Murata, C. et al., "Improvement of fluorescence characteristics of coumarins: Syntheses and fluorescence properties of 6-methoxycoumarin and benzocoumarin derivatives as novel fluorophores emitting in the longer wavelength region and their application to analytical reagents," *Chem. Pharm. Bull.*, vol. 53, No. 7, pp. 750-758 (2005).
Whitaker, J. et al., "Spectral and photophysical studies of benzo[c]xanthene dyes: Dual emission pH sensors," *Anal. Biochem.*, vol. 194, pp. 330-344 (1991).
Xie, W. et al., :"A nondoped-type small mo9lecule white organic light-emitting device," *J. Phys. D: Appl. Phys.*, vol. 36, pp. 1246-1248 (2003).
Yang, Y., "A near-infrared emission xanthene exhibiting a substantial Stokes shift" (manuscript 2007).
Yang, Y. et al., "An organic white light-emitting fluorophore," *J. Am. Chem. Soc.*, vol. 128, pp. 14081-14092 (2006), including supplemental information available on the web, and with a correction, vol. 129, pp. S1-S37 (2007).
Yang, Y. et al., "A convenient preparation of xanthene dyes," *J. Org. Chem.*, vol. 70, pp. 6907-6912 (2005).

*Primary Examiner* — Bernard Dentz
(74) *Attorney, Agent, or Firm* — John H. Runnels; Bonnie J. Davis

(57) ABSTRACT

Xanthene compounds are disclosed having fluorescence at multiple wavelengths. Also disclosed are methods for their synthesis and use. Some of the compounds fluoresce at three wavelengths, emitting white light. Uses include the imaging of biological tissues, illumination, and display technologies. Many of the compounds have large Stokes shifts, and are resistant to photobleaching. The fluorescence may be readily distinguished from that of endogenous fluorophores, and from that of most existing, commercially-available fluorescent probes. The compounds are well suited for use in "multiplexing" techniques. They exhibit clear isosbestic and isoemissive points, and have broad absorption and emission ranges.

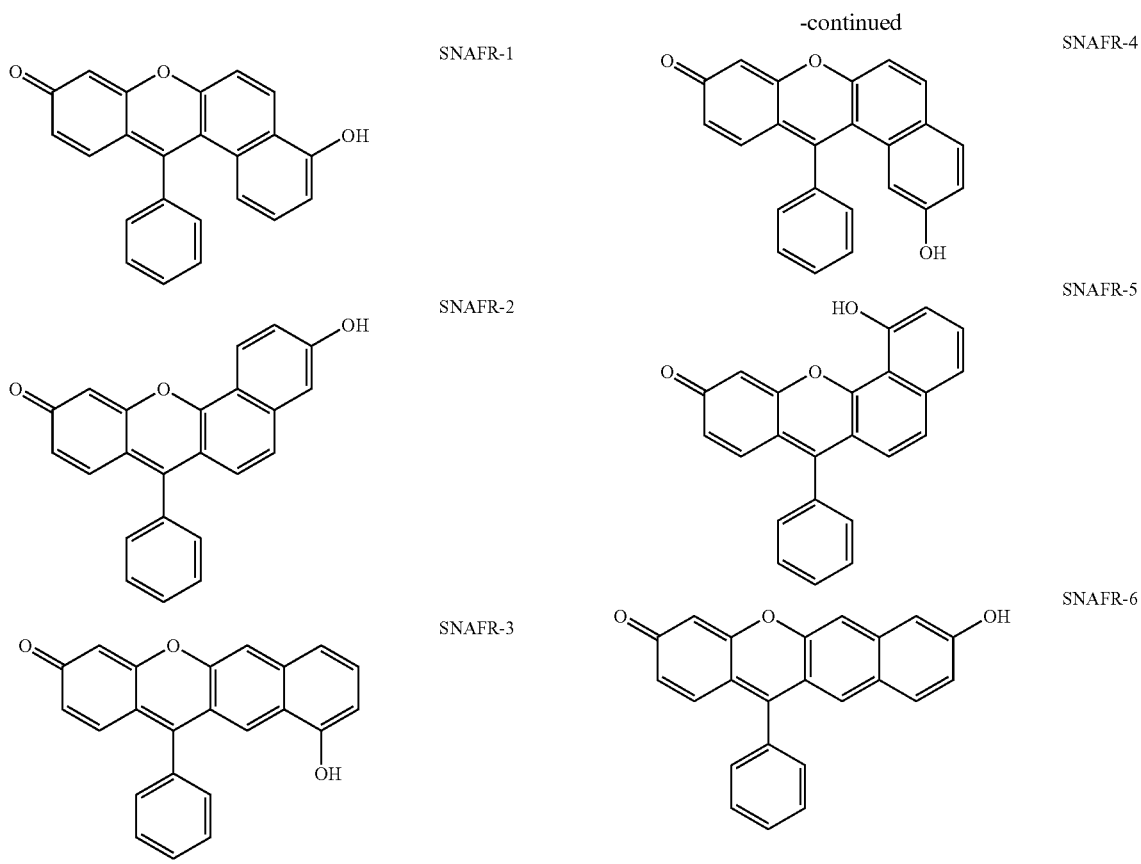
9 Claims, 26 Drawing Sheets xanthene benzo[c]xanthene benzo[b]xanthene benzo[a]xanthene

FLUORESCENT XANTHENES AND WHITE LIGHT FLUOROPHORES

This is the United States national stage of international application PCT/US2007/073864, international filing date 19 Jul. 2007, which claims the benefit of the 21 Jul. 2006 filing date of U.S. provisional patent application 60/832,413 under 35 U.S.C. §119(e).

The development of this invention was partially funded by the United States Government under grant R01 EB002044 awarded by the National Institutes of Health. The United States Government has certain rights in this invention.

TECHNICAL FIELD

This invention pertains to novel fluorescent xanthene molecules and their uses. The dyes typically fluoresce at multiple wavelengths. For example, some of the novel molecules fluoresce at three wavelengths upon UV excitation, emitting light that appears close to a natural white to the human eye. Only a discrete handful of molecules have previously been reported that will fluoresce white light, and none of them are closely related chemically to the novel compounds disclosed here. Uses include, e.g., imaging of biological tissues, illumination, and display technologies. The novel fluorescence may be used to replace illumination devices such as incandescent bulbs, fluorescent lamps, and light-emitting diodes. They may be used in display technologies such as flat panel liquid crystal displays, plasma displays, and "electronic paper." They may be used as labels for biomolecules, and are particularly useful in ratiometric techniques. Some of the novel compounds are also useful as near-infrared fluorophores.

BACKGROUND ART

Fluorescent molecules or fluorophores have many uses, including optical detection, identification, and quantification of complex biological structures such as the constituents of living cells. Fluorophores are widely used in biochemical studies and in clinical diagnoses. Many fluorophores are polyaromatic or heterocyclic hydrocarbons. Their differential partitioning among cell constituents allows one to image cellular components that are otherwise difficult to visualize.

A fluorophore will absorb a photon of energy $E_{ex}=h\nu_{ex}=hc/\lambda_{ex}$, where h denotes Planck's constant, c is the speed of light, and $\nu_{ex}$ and $\lambda_{ex}$ are the frequency and wavelength of the absorbed light, respectively. A fluorophore typically stays in the excited electronic state for about 1 to 10 nanoseconds. During this time some of the absorbed energy is transferred to other molecules via collisions, and some is dissipated into the molecule's own vibrational and rotational modes. The excited molecule enters a lower electronic energy state as energy dissipates. The molecule then emits a lower-energy photon as it returns to its electronic ground state. The difference between the wavelength of absorption and emission is called the "Stokes shift" $\lambda_{em}-\lambda_{ex}$.

The quantum-mechanical and classical processes underlying fluorescence and the Stokes shift are statistical in nature, meaning that fluorescence emission does not occur at a single wavelength, but instead occurs over a spread of wavelengths around a peak fluorescence intensity $\lambda_{em}$. Similar statistical considerations apply to absorption. Absorption occurs over a spread of wavelengths around one or more resonant wavelength peaks $\lambda_{res}$. The Stokes shift $\lambda_{em}-\lambda_{ex}$ represents the difference between the absorption resonance maximum and the fluorescence peak maximum.

It is generally preferred to have a Stokes shift large enough that overlap of the excitation and fluorescence peaks is negligible. Where this condition is satisfied, appropriately-colored optical filters, monochromators, or the like may be used to discriminate between Rayleigh-scattered incident light and fluorescence from the probe molecule. This can be an important practical experimental consideration, because illumination of the specimen can be very intense in comparison to the strength of the emitted fluorescent signal. Without the ability to sharply discriminate between excitation and emission wavelengths, scattered illumination can saturate the detector, making fluorescence measurements difficult or even impossible.

The extreme sensitivity of fluorescence techniques depends on the capacity of a fluorophore to respond to intense illumination by repeating the excitation/emission cycle very rapidly, perhaps millions of times each second. "Photobleaching" can disrupt the cycle by destroying the fluorophore, for example, when an excited fluorophore breaks apart or undergoes an irreversible chemical reaction. Another preferred property of a fluorophore is resistance to photobleaching.

Another property affecting a fluorophore's usefulness is its molecular weight. All else being equal, it is generally the case that cell membranes are less permeable to larger fluorophores. In general, lower molecular-weight fluorophores will more readily enter cellular substructures, or traverse the blood/brain barrier. On the other hand, the total number of vibrational and rotational modes available to a photoexcited dye to dissipate energy tends to decrease dramatically with decreasing molecular weight. Smaller fluorophores thus tend to have smaller Stokes shifts, which in turn can make it more difficult to resolve scattered excitation radiation from true fluorescence, especially with a low fluorescence signal. It is highly desirable to have low molecular-weight fluorophores with large Stokes shifts.

The emission and absorption spectra of some fluorophores are sensitive to their chemical environment. For instance, the presence of $Ca^{2+}$ causes "fura-2" and "indo-1" dyes to fluoresce at different wavelengths, allowing them to be used for in situ intracellular $Ca^{2+}$ assays. Many dyes have carboxylic acid or amine groups that undergo ionization with a pH change; these ionizations create a change in fluorescence.

Dual fluorescence is known in a number of compounds, but very few previously reported compounds have demonstrated three-color fluorescence. Multi-color fluorescence is useful in "ratiometric" techniques. The combined fluorescence intensities from the different peaks provide a measure of the total amount of fluorophore present. The intensity ratios of the peaks are an indicator of the environmental conditions to which the fluorophore is sensitive, for example pH or $Ca^{+2}$ concentration. Normalization of these measurements can sometimes be helpful, as the fluorophore concentration can vary—whether randomly, or as a consequence of the process under study, or as the result of photobleaching. Monitoring fluorescence intensities and ratios at multiple wavelengths can resolve ambiguities that would exist from measurements at just a single wavelength. Ratiometric techniques have been used for purposes such as determining intracellular pH, microviscosity, flow cytometry, and confocal microscopy.

Dual fluorescence has been reported in some compounds, including 4-(N,N-dimethylamino)-benzonitrile and analogues, biaryls, benzo[c]xanthenes, 3-hydroxyflavones, hydroxy-camptothecin, 6-hydroxyquinoline-N-oxides, aromatic dicarboximides, carotenoids, and 1,3-diphenyl-1H-pyrazolo[3,4-b]-quinoline.

Another preferred property of a fluorophore is that the fluorescence should be resolvable not only from the excitation wavelength $\lambda_{ex}$, but also from any fluorophores that are endogenous to the specimen.

There is also a need for new fluorophores whose fluorescence may readily be distinguished from that of existing, commercial, fluorescent probes, so that the new probe may be used concurrently with existing probes in "multiplexing" techniques, the simultaneous monitoring of different biochemical or other functions with dyes possessing different membrane permeabilities, pH sensitivities, or other sensitivities.

Dyes that are active in near infrared (NIR) wavelengths have found many uses. There is relatively little interference from endogenous absorption or fluorescence in biological samples in the near infrared. Rayleigh scattering at NIR-wavelengths is low compared to visible light scattering. NIR can penetrate tissue to a greater depth. However, there are relatively few classes of NIR dyes currently available. Those that are available include phthalocyanines, cyanines, and squaraines. There is a continuing unfilled need for novel NIR fluorescent dyes.

Some NIR dyes have been modified with various functional groups to change their properties, but adding functional groups has generally been at the expense of lower quantum yields. Modifications also generally increase the molecular weight, which can interfere with the functions of biomolecules, or with a fluorophore's ability to cross cellular or sub-cellular membranes, or with its solubility. Some modifications will cause a dye to precipitate, rendering it useless for many purposes.

Phthalocyanine and squaraine dyes in biological systems often tend to precipitate or to aggregate. Squaraines can also be chemically reactive.

Cyanine dyes possess excellent NIR properties and have high molar absorptivities, adequate fluorescence, and good photostability. However, their intrinsically small Stokes shifts can make it difficult to resolve the fluorescence emission signal of a cyanine dye from the exciting radiation, or from scattered light.

L. Lee et al., *Cytometry*, 1989, vol. 10, 151-164 disclosed structures for benzo[a]xanthene and benzo[b]xanthene, but did not disclose a synthesis for either, nor any use for the hypothesized compounds. This work described a synthesis for a benzoxanthene starting from 1,6-dihydroxynaphthene and other reagents. After the synthesis was concluded, NMR measurements led to the conclusion that the benzo[c]xanthene isomer was the one that had in fact been made, not the benzo[a]xanthene or the benzo[b]xanthene isomer. See FIG. 12 of the present application, in which R designates an alkyl or aryl group.

W. Fabian et al., *J. Chem. Soc, Perkin Trans.* 2, 1996, 5, 853-856 described the results of semi-empirical calculations on three classes of regioisomers. The authors concluded on theoretical grounds that the benzo[a]- and benzo[b]-isomers should absorb and emit at a significantly longer wavelengths than other isomeric benzo- or naphthofluoresceins The authors further suggested that these molecules might be used as intracellular pH probes. However, no source, synthetic scheme, or other method of obtaining the [a] or [b] benzoxanthene isomers molecules was described or suggested. Nor, to the present inventors' knowledge, has any other prior report described or suggested any such source, synthetic scheme, or other method for obtaining these molecules. Technically, developing a synthetic route to the [a] and [b] isomers is more challenging because the nucleophilic carbon corresponding to the path to the [c] isomer is the most electron-rich of the three potential nucleophilic carbon atom sites.

C. Murata et al., "Improvement of fluorescence characteristics of coumarins: Syntheses and fluorescence properties of 6-methoxycoumarin and benzocoumarin derivatives as novel fluorophores emitting in the longer wavelength region and their application to analytical reagents," *Chem. Pharm. Bull.*, vol. 53, pp. 750-758 (2005) discloses the synthesis of various 3-substituted-6-methoxycoumarin derivatives, benzocoumarin derivatives, and their fluorescence properties and Stokes shifts.

Benzo[c]xanthenes have been reported to exhibit dual ratiometric fluorescence, to have well-resolved emission bands at relatively long wavelength absorptions and emissions, and to have near-neutral $pk_a$'s. They also exhibit clear isosbestic and isoemissive points. J. Whitaker et al., "Spectral and photophysical studies of benzo[c]xanthene dyes: Dual emission pH sensors," *Anal. Biochem.*, vol. 194, pp. 330-344 (1991) discloses a series of long-wavelength, benzo[c]xanthene dyes, their dual fluorescent emission bands, and their use in pH measurements.

C. Chang et al., "A tautomeric zinc sensor for ratiometric fluorescence imaging: Application to nitric oxide-induced release of intracellular zinc," *Proc. Natl. Acad. Sci. USA*, vol. 101, pp. 1129-1134 (2004) discloses a tautomeric seminaphthofluorescein probe and its use in the intracellular, dual-emission, ratiometric, fluorescent, selective imaging of $Zn^{2+}$.

Multi-color fluorescence allows one to create a range of emission colors, as perceived by the human eye. For example, equal mixing of red and green is perceived as yellow. Traditional methods for the fluorescent generation of white light generation have typically mixed different compounds emitting at three different frequencies, such as a mixture of separate red, green, and blue fluorophores.

There have been a few prior reports of single-component white-light emitters. None are closely related chemically to the novel compounds disclosed here. For example, M. Bowers et al., *J. Am. Chem. Soc.* 2005, 127, 15378-15379 disclose white light, broadband photoluminescence from cadmium selenide nanocrystals.

K. Hutchison et al., *J. Am. Chem. Soc.*, 1999, 121, 5611-5612 disclose white-light electroluminescence from a fullerene adduct.

Y. Liu et al., *J. Am. Chem. Soc.*, 2006, 128, 5592-5593 disclose white-light electroluminescence from a carbazole-substituted aromatic enyne.

W. Xie et al., *J. Phys. D: Appl. Phys.* 2003, 36, 1246-1248 disclose a white light-emitting device whose structure included indium tin oxide glass substrate/50 nm N,N'-bis-(1-naphthyl)-N,N'-diphenyl-1,1'-biphenyl-4,4'-diamine hole transporting layer/0.05 nm 4-(dicyano-methylene)-2-methyl-6-(p-dimethylaminostyryl)-4H-pyran/25 nm 4,4'-bis(2, 2'diphenylvinyl)-1,1'-biphenyl/15 nm tris(8-hydroxyquinoline) aluminum electron transporting layer/0.5 nm lithium fluoride/aluminum.

W. Jia et al., *Chem. Mater.* 2005, 17, 164-170 disclose an electroluminescent blue emitter molecule that contains part of the N,N'-di-1-naphthyl-N,N'-diphenylbenzidine functionality, and a three-coordinate boron center. There was a substantial shift in the wavelength of maximum emission in different solvents.

P. Furuta et al., *J. Am. Chem. Soc.*, 2004, 126, 15388-15389 disclose white-light electroluminescence from a platinum-functionalized random copolymer.

Y. Liao, *J. Am. Chem. Soc.*, 2005, 127, 9986-9987 disclose white-light photoluminescence from microporous zinc gallophosphate.

K. Hutchinson et al., *J. Am. Chem. Soc.*, 1999, 121, 5611-5612 disclose a white light-emitting diode fabricated by blending a $T_h$-hexapyrrolidine $C_{60}$ adduct with poly(9-vinylcarbazole) and 2,5-bis-(4-naphthyl)-1,3,4-oxadiazole.

DISCLOSURE OF INVENTION

We have discovered novel, multi-wavelength fluorescence compounds, methods for their synthesis under relatively mild conditions, and methods for their use. The dyes typically fluoresce at multiple wavelengths. Some of the novel molecules have the unique, highly unexpected property of fluorescing at three wavelengths upon UV excitation, thereby emitting white light, light that appears as a nearly natural white to the human eye. Uses include the imaging of biological tissues, illumination, and display technologies. The novel fluorescence may be used to replace illumination devices such as incandescent bulbs, fluorescent lamps, and light-emitting diodes. They may be used in display technologies such as flat panel liquid crystal displays, plasma displays, and "electronic paper."

The novel compounds generally have large Stokes shifts. They are generally resistant to photobleaching. The fluorescence may be readily distinguished from that of endogenous fluorophores, and from that of most existing, commercially-available fluorescent probes. The new compounds are well suited for use in "multiplexing" techniques. They exhibit clear isosbestic and isoemissive points, and have broad absorption and emission ranges. These compounds may be modified with other functional groups, or incorporated into polymers.

The novel Compounds include those having a structure selected from the group consisting of:

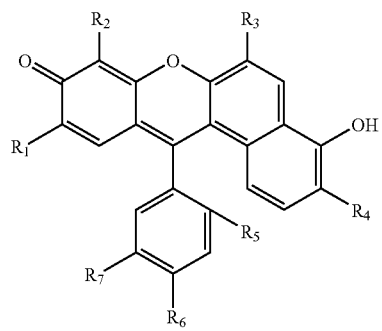

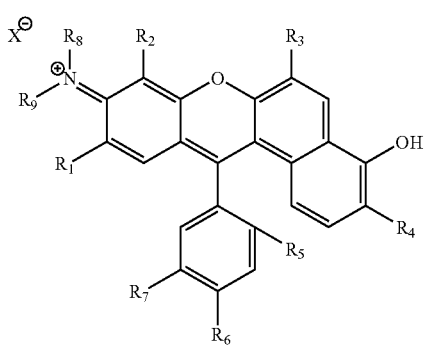

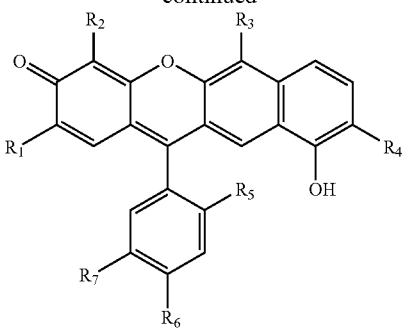

-continued

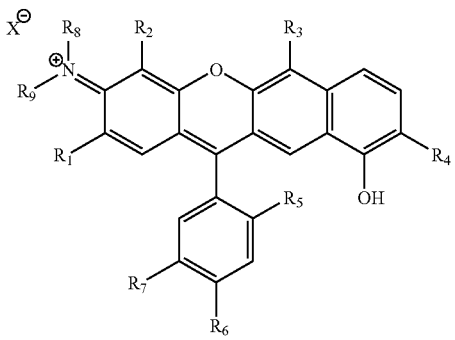

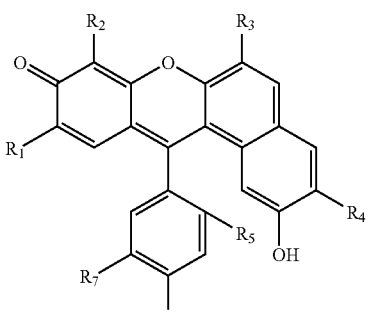

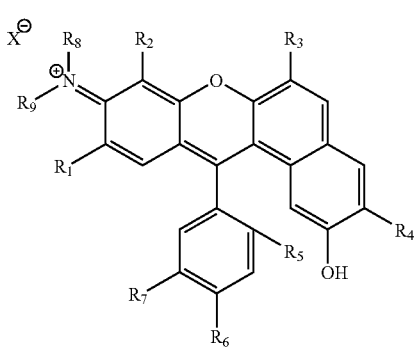

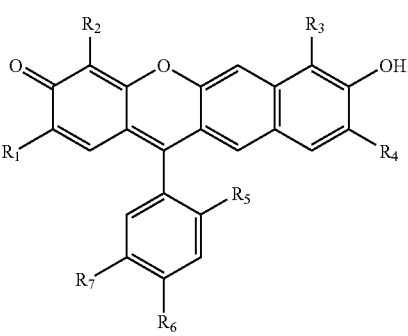

-continued

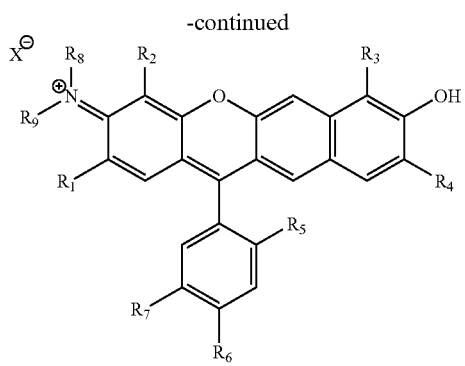

wherein:

R1, R2, R3, R4, R6, and R7 are each independently selected from the group consisting of H, $C_1$ to $C_4$ substituted or unsubstituted alkyl, $C_6$ to $C_{10}$ aryl, $C_1$ to $C_4$ alkenyl, $C_1$ to $C_4$ alkynyl, substituted or unsubstituted amino, halide, hydroxyl, $C_1$ to $C_4$ alkoxy, thio, nitro, $C_1$ to $C_4$ aldehyde, acetyl, $C_1$ to $C_4$ carboxyl, $C_1$ to $C_4$ alkoxycarbonyl, and $C_1$ to $C_4$ alkylaminocarbonyl;

R5 is selected from the group consisting of H, $C_1$ to $C_4$ alkyl, $C_1$ to $C_4$ carboxyl, $C_1$ to $C_4$ alkoxycarbonyl, and $C_1$ to $C_4$ alkylaminocarbonyl;

R8 and R9 are each independently selected from the group consisting of H, and $C_1$ to $C_4$ alkyl; and X is selected from the group consisting of F, Cl, Br, I, $CF_3COO$, and $PF_6$.

Examples of the novel compounds include SNAFR-1, SNAFR-2, SNAFR-3, SNAFR-4, SNAFR-5, and SNAFR-6, whose structures are depicted in FIG. 13. To date the SNAFR-1, SNAFR-2, SNAFR-3, SNAFR-4, and SNAFR-6 embodiments have been synthesized. SNAFR-1, SNAFR-2, SNAFR-4, and SNAFR-6, in DMSO with 1% phosphate buffer, all showed three-color emission when excited in UV.

"SNAFR" (seminaphthofluorone) fluorescence typically changes when the carboxylic acid group deprotonates with increasing pH, for example from a green 540 nm emission to a red 620 nm emission. In an intracellular environment, the ratio of red to green fluorescence peaks corresponds to the ratio of unionized and ionized fluorophores, and thus to the pH of the immediate environment.

The novel fluorophores possess high extinction coefficients, and very broad absorption ranges. SNAFR-2, for example, can be excited over a range of some 400 nm from the UV to deep red. SNAFR-2 in solution simultaneously fluoresces red, green, and violet, producing a nearly-white light.

SNAFR-6 exhibits a Stokes shift of ~200 nm. It may be excited over a wide range of the visible spectrum, and also emits into the NIR region. It is particularly useful for multiplexing fluorescence applications. It may be excited at the same wavelengths as many currently-used, commercially available dyes, but its emission is readily resolved from that of most existing dyes.

Xanthene dyes are typically synthesized via an acid-catalyzed condensation between resorcinol and a reactant such as a phthalic anhydride, an acid chloride, an ester, or an aldehyde. It is known in the art that by replacing resorcinol with 1,6-dihyxdroxynaphthalene, under classical acid-catalyzed thermal conditions, benzo[c]xanthene is formed. However, these thermal oxidative conditions usually produce low yields. Also, there can be significant problems in purifying the product due to the formation of chemically similar, polar by-products.

We have found synthetic methods to readily produce regioisomerically pure xanthene dye derivatives, such as benzo[a]xanthene and benzo[b]xanthene, via methylated carbinol intermediates, followed by demethylation and condensation. A tertiary carbinol leuco base is made via a Grignard reaction. Treating the carbinol leuco base with $BBr_3$ produces the novel dyes. The products are purified, for example, by column chromatography. Some of the dye products can be purified by simple filtration methods, without requiring chromatographic separation. The novel, low temperature, basic method avoids the potentially troublesome oxidation reactions that have previously been used to produce xanthene dyes.

MODES OF CARRYING OUT THE INVENTION

Examples 1-3

Figure 14:
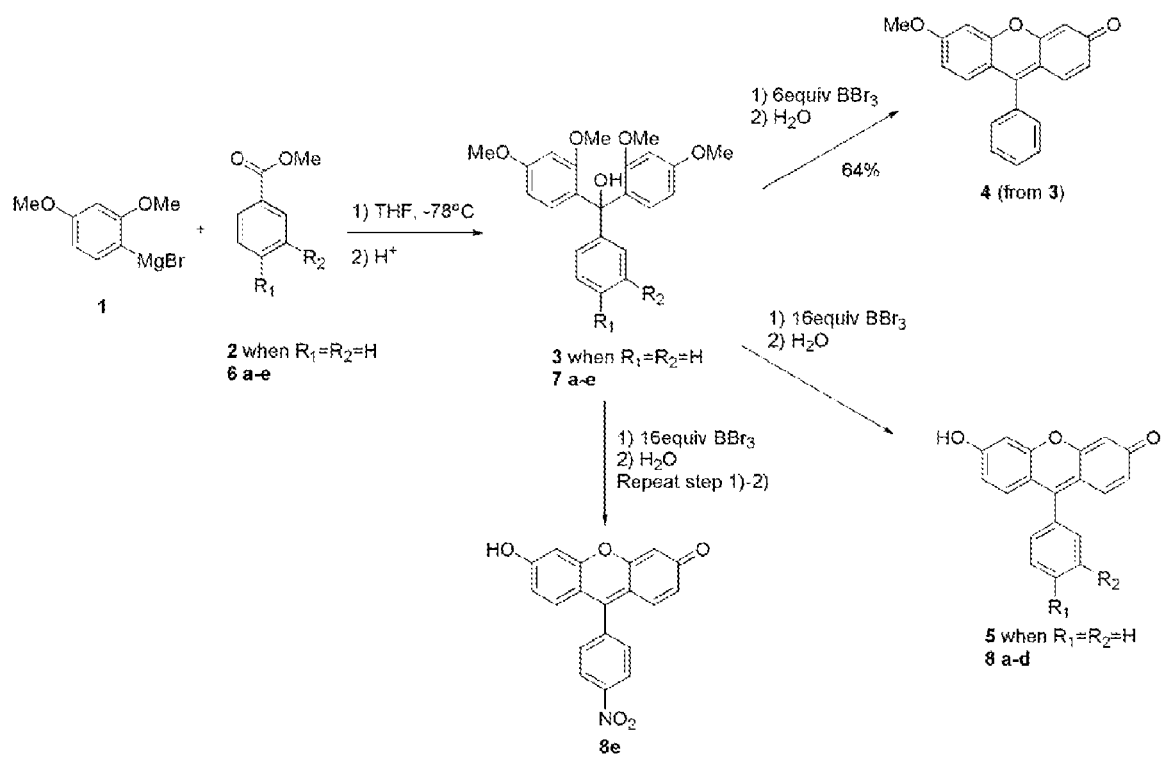
FIG. 14 depicts a synthetic scheme for Compounds 3, 4, 5, 7a-e, 8a-e, and a generic reaction scheme for related Compounds.
Figure 14:
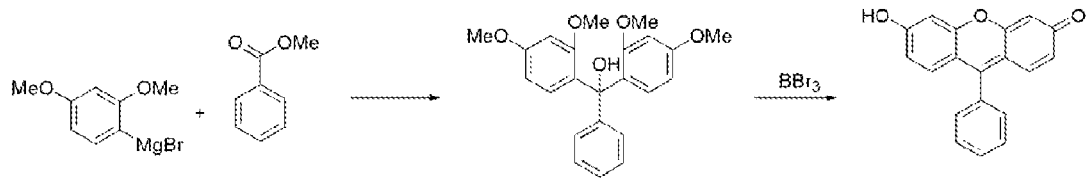
Figure 15:
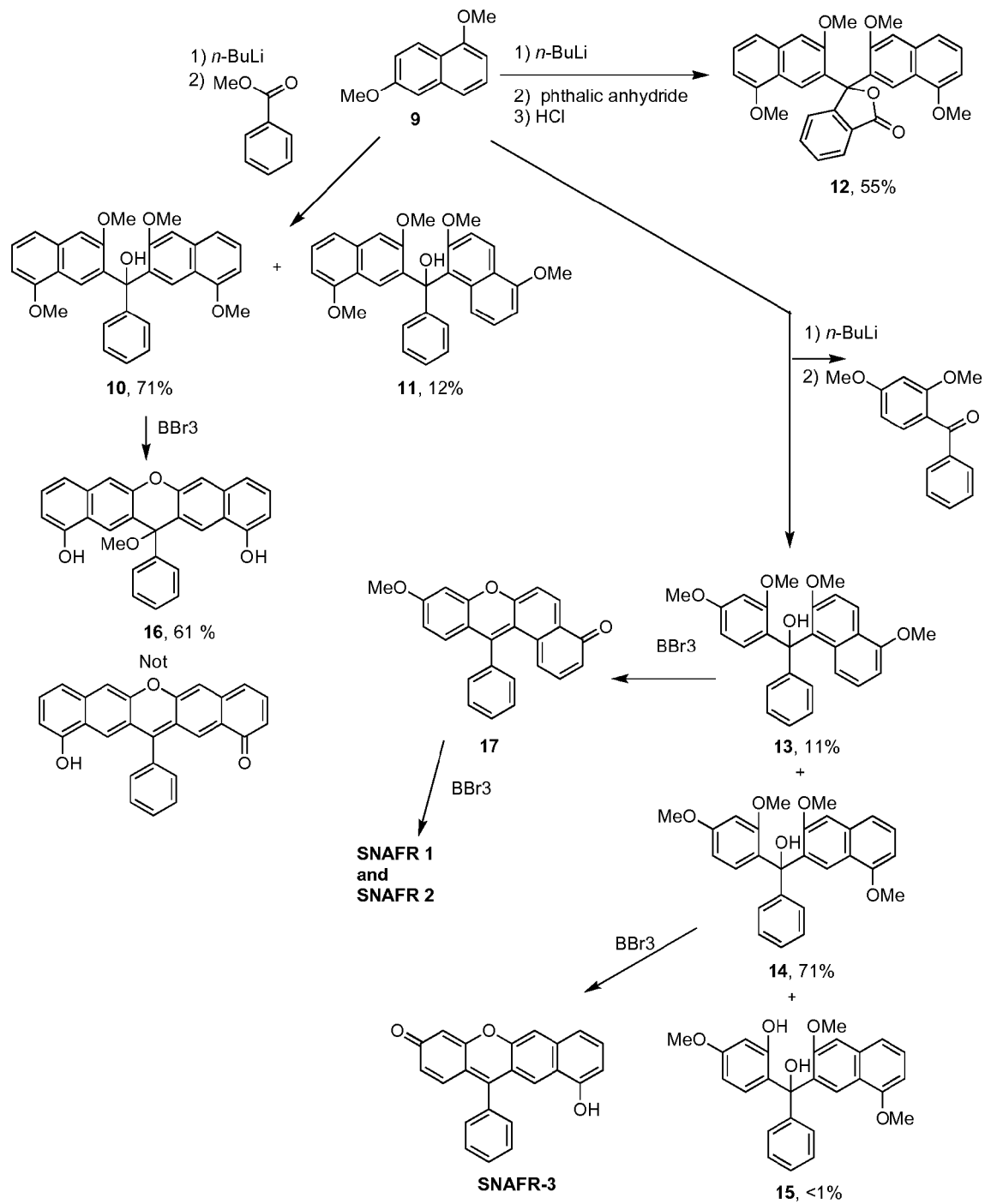
FIG. 15 depicts a synthetic scheme for Compounds 10, 11, 12, 13, 14, 15, 16, and 17, and for SNAFR-1, SNAFR-2, and SNAFR-3.

Synthetic reaction schemes useful in making Compounds within the scope of this invention are depicted in FIGS. 14 and 15. Compound 3 was obtained in one step in a yield of 96% by reacting 2,4-dimethoxybenzenemagnesium bromide 1 and methyl benzoate 2. The structure of Compound 3 was confirmed by X-ray crystallography (data not shown). When Compound 3 was treated with $BBr_3$ (6 equiv), monomethylether 4 was obtained in 64% yield. Using a greater excess of $BBr_3$ (16 equiv) produced fully deprotected Compound 5 in 65% yield. Compound 5 was readily isolated by simple filtration.

Examples 4-14

The synthetic scheme was readily modified to synthesize a series of regioisomerically-pure fluorone dyes. When various methyl benzoates 6a-e were used, the corresponding carbinols 7a-e were obtained in excellent yields (>90%). The reaction of the carbinols 7a-d with 16 equiv $BBr_3$ produced fluorone dyes 8a-d at yields of 70%-88%. Using excess $BBr_3$ produced fluorone 8e in good yield. In each case, the fluorone products 8 were obtained without the need for preparative chromatography. The structures of Compounds 7b and 7e were confirmed by single crystal X-ray structure analysis. See Table 1.

TABLE 1

| Entry | Substrate | $R_1$ | $R_2$ | Carbinol | Carbinol yield (%) | Fluorone | Fluorone Yield (%) |
|---|---|---|---|---|---|---|---|
| 1 | 6a | Br | H | 7a | 92 | 8a | 70 |
| 2 | 6b | Ph | H | 7b | 99 | 8b | 87 |
| 3 | 6c | OMe | H | 7c | 83 | 8c | 96 |
| 4 | 6d | H | $NO_2$ | 7d | 91 | 8d | 73 |
| 5 | 6e | $NO_2$ | H | 7e | 95 | 8e | 65 |

Note:
The 65% fluorone yield in row 5 denotes the overall yield following a two-step demethylation sequence.

Examples 15-20

When a solution of lithiated Compound 9 was reacted with methyl benzoate, we obtained Compounds 10 and 11 in yields of 71% and 12%, respectively. When phthalic anhydride was used in place of methylbenzoate, Compound 12 was obtained in 55% yield. When lithiated 1,6-dimethoxynaphthalene was reacted with Compound 2,4-dimethoxybenzophenone, Compounds 13 and 14 were isolated in 11% and 71% yields, respectively. Trace amounts of Compound 15 were also produced, presumably due to trace amounts of 2-hydroxy-4-methoxybenzophenone in the reaction mixture from incomplete methylation of 2,4-dihydroxybenzophenone. Single crystal X-ray structure analysis confirmed the assigned structures of Compounds 10-15.

Examples 21-25

Using $BBr_3$ to demethylate Compound 10, we obtained compound 16 in 61% yield. Using $BBr_3$ to demethylate Compound 13, Compound 17 was obtained quantitatively. Reacting Compound 17 with 20 equiv $BBr_3$ produced a mixture of SNAFR-1 and SNAFR-2. Using $BBr_3$ to demethylate Compound 14, SNAFR-3 was produced in a yield of 15%. The structures of Compound 16 and SNAFR-3 were confirmed by single crystal X-ray structural analysis (data not shown).

Example 26

Figure 16:
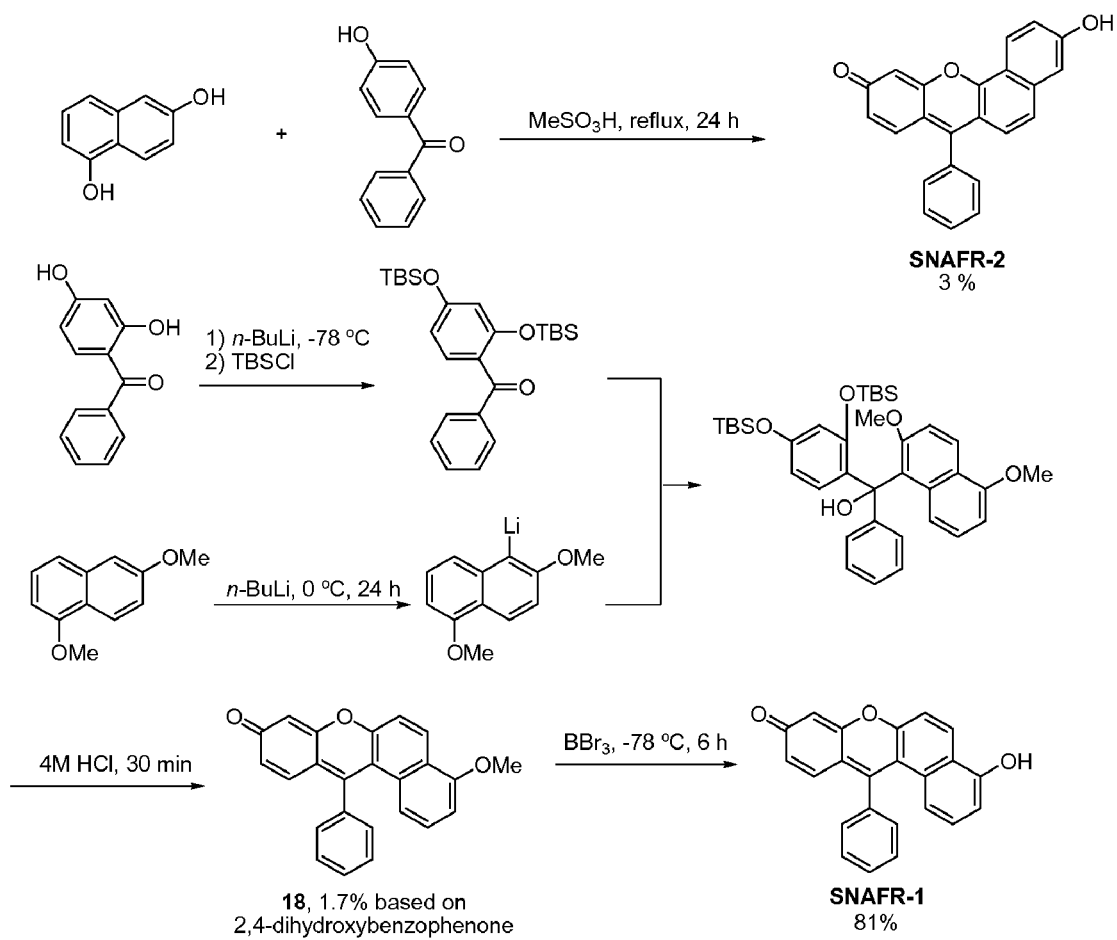
FIG. 16 depicts alternate synthetic schemes for SNAFR-1 and SNAFR-2.
Figure 17:
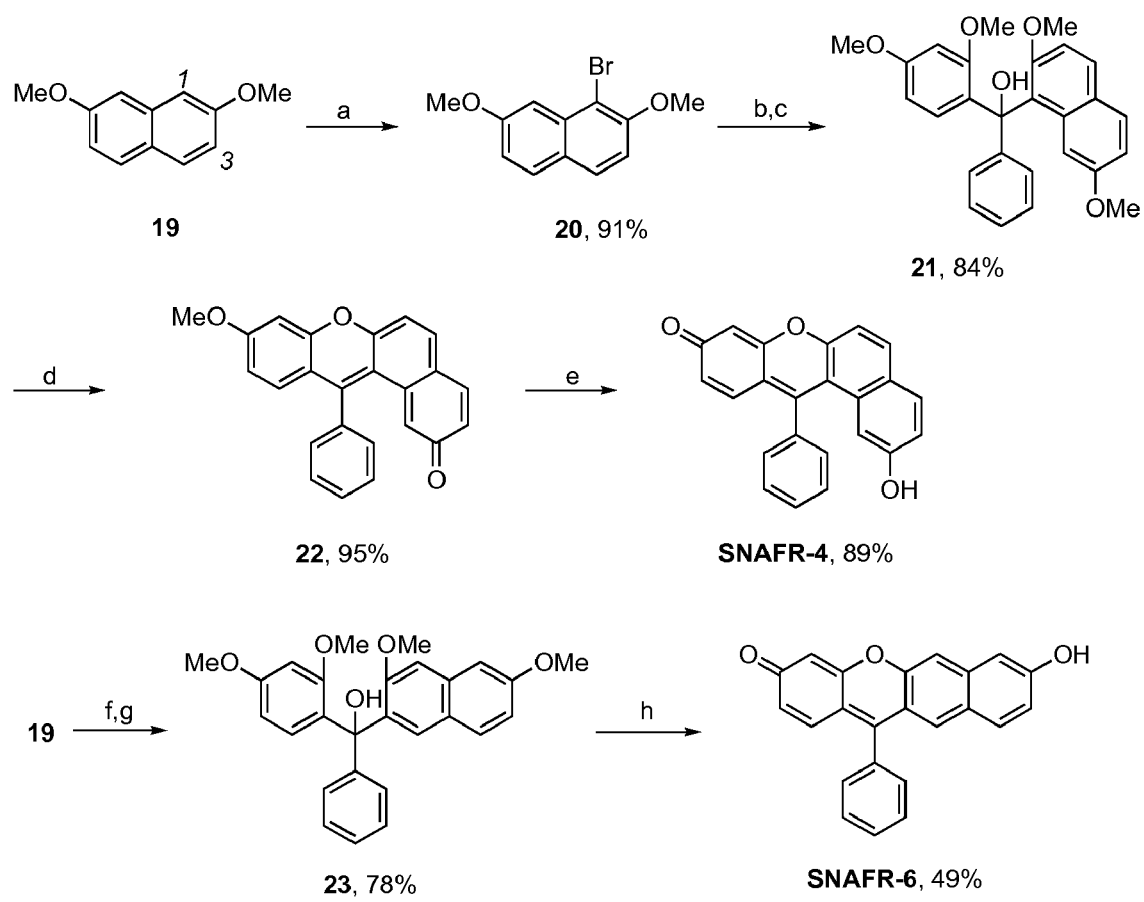
FIG. 17 depicts synthetic schemes for Compounds 20, 21, 22, and 23, and for SNAFR-4 and SNAFR-6.

We also developed alternative synthetic routes to prepare both SNAFR-1 and SNAFR-2. See FIG. 16.

Alternative Synthesis of SNAFR-1.

2,4-Dihydroxybenzophenone (2.0 g, 9.3 mmol) was dissolved in THF (100 mL). The solution was cooled to −78° C. in a dry ice bath. n-BuLi (11.6 mL, 1.6 M in hexane) was added drop-wise with constant stirring. The mixture was allowed to warm to room temperature overnight, and then cooled to 0° C. in an ice bath. Then t-butyldimethylsilyl chloride (2.9 g, 19.5 mmol) in THF (20 mL) was added drop-wise. After the addition was complete, the solution was allowed to warm to room temperature over 4 hours. The solution was cooled to −78° C., and a solution of lithiated 1,6-dimethoxynaphthalene (1.84 g, 9.8 mmol) was added drop-wise. The solution was then allowed to warm to room temperature overnight. HCl (10 mL, 4 M) was added in a single portion. The solution was stirred at room temperature for 30 min. Deionized $H_2O$ (200 mL) was added. Most of the THF was then removed under vacuum. The remaining aqueous material was extracted with $CH_2Cl_2$ and dried over $MgSO_4$. Purification by flash chromatography (EtOAc) produced 56 mg (1.7% yield, based on 2,4-dihydroxybenzophenone) of SNAFR-1 methyl ether, Compound 18. Then 18 mg of Compound 18 was dissolved in anhydrous $CH_2Cl_2$. The solution was cooled in a dry ice bath. Then 0.3 mL $BBr_3$ was added to demethylate Compound 18 to obtain 14 mg (81% yield) of SNAFR-1.

Example 27

Alternative Synthesis of SNAFR-2

1,6-Dihydroxynaphthalene (1.5 g, 9.3 mmol) and 2,4-dihydroxybenzophenone (2.0 g, 9.3 mmol) were added to a 100 mL round bottom flask containing 25 mL $CH_3SO_3H$. The mixture was heated to reflux for 24 h. The resulting dark-red liquid was poured into 200 mL distilled $H_2O$, and neutralized by adding $NaHCO_3$ until the solution turned almost colorless. The supernatant was decanted, and the residue was dissolved in MeOH and treated with $Na_2SO_4$. The mixture was filtered and evaporated to dryness. The red residue was purified by flash chromatography (EtOAc:MeOH, 9.5:0.5). SNAFR-2 was obtained, 18.6 mg (3% yield).

Examples 28-30

Synthesis of SNAFR-4 and SNAFR-6

Compound 19, 2,7-dimethoxynaphthalene was treated with $Br_2$ at room temperature, The C-1 carbon was brominated selectively to produce Compound 20 in 91% yield. Compound 20 was then converted to the corresponding Grignard reagent. Reaction with 2,4-dimethoxybenzophenone produced Compound 21 in 84% yield. Demethylation of Compound 21 produced Compound 22 in near-quantitative yield. Further demethylation of Compound 22 produced SNAFR-4 in 89% yield. When Compound 19 was treated with n-BuLi at room temperature, the C-3 carbon was lithiated. Nucleophilic attack at 2,4-dimethoxybenzophenone produced Compound 23 in 78% yield. SNAFR-6 was readily prepared from Compound 23 in 49% yield by demethylation.

Use of SNAFR-2 in Ratiometric pH Fluorometry

Example 31

Figure 1A:
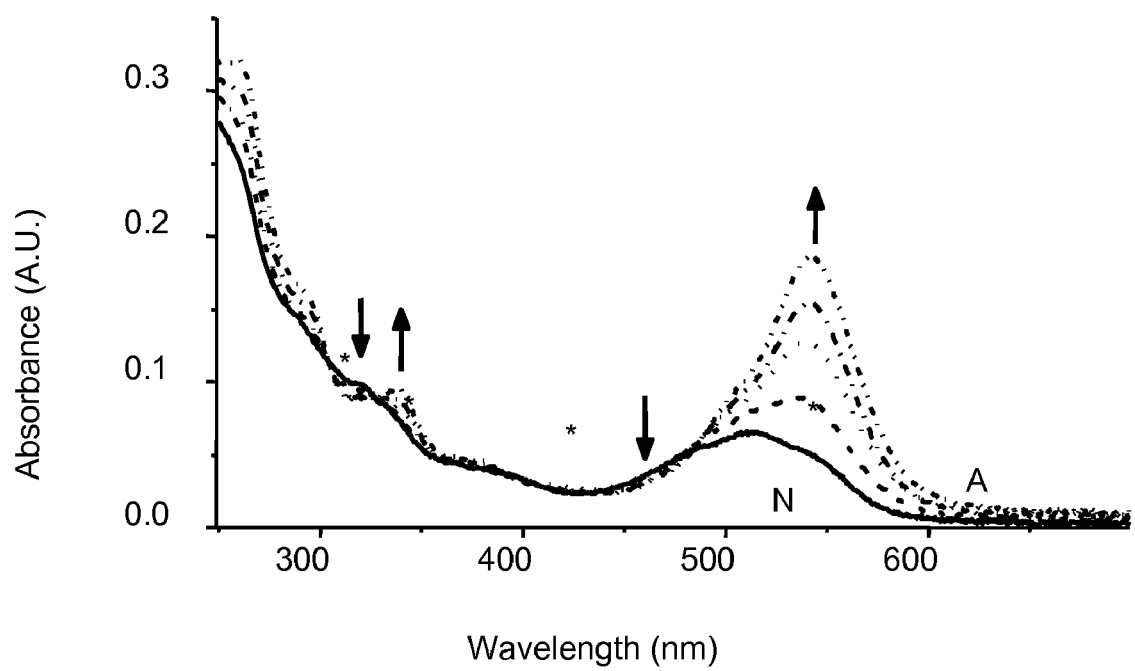
FIGS. 1A-1H and FIGS. 2A-2I depict spectral properties of 30 μM SNAFR-2 in 50 mM phosphate buffer with 0.25% DMSO at various pH values.

UV-Visible Absorption Properties of SNAFR-2 as a Function of pH in 0.25% DMSO in Phosphate Buffer Solution Absorption spectra of SNAFR-2 as a function of pH are shown in FIG. 1A. SNAFR-2 was dissolved in 50 mM phosphate buffer with 0.25% DMSO. As the pH increased, the absorption band centered at 550 nm increased. We attributed this band to the anionic form (A). Concurrently, the absorption band at ca. 460 nm decreased. We attributed the 460 nm band to the neutral form (N). Four isosbestic points were observed, at 484, 394, 327, and 304 nm. The 484 nm isosbestic point is near the 488 nm Ar ion laser line. Thus ratiometric measurements using SNAFR-2 as a probe may be conducted with an Ar ion laser and common, commercially available filter sets.

Example 32

Fluorescence Properties of SNAFR-2 as a Function of pH in 0.25% DMSO in Phosphate Buffer Solution Other benzoxanthenes have been previously reported to have dual fluorescence emission bands, with intensities that are pH-dependent. SNAFR-2 also exhibited dual emission bands. The emission bands were pH-sensitive.

Figure 1B:
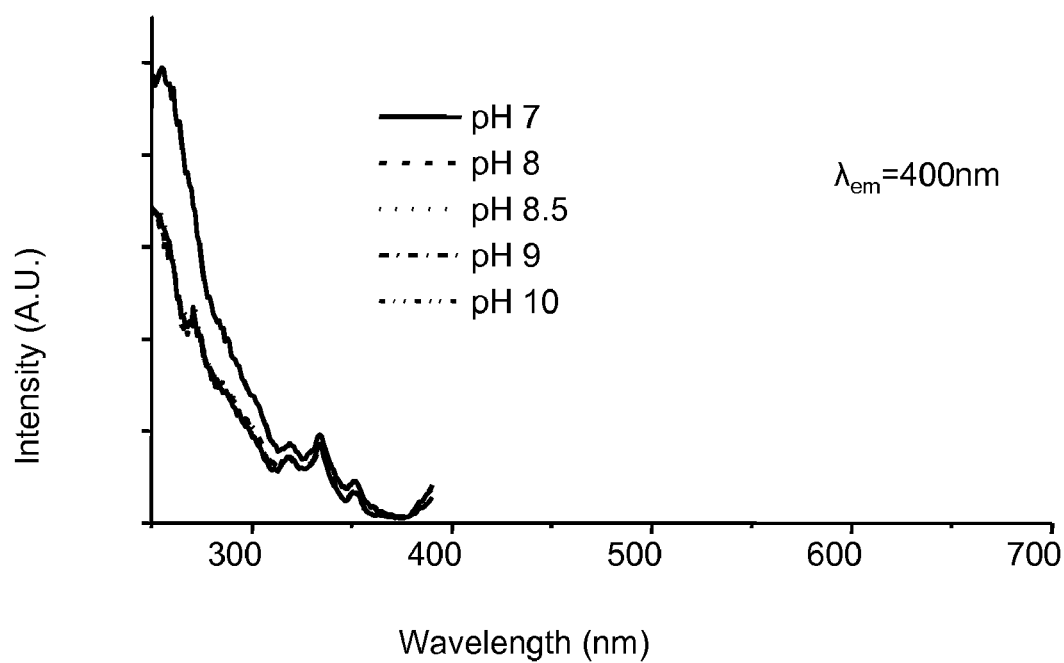
Figure 1C:
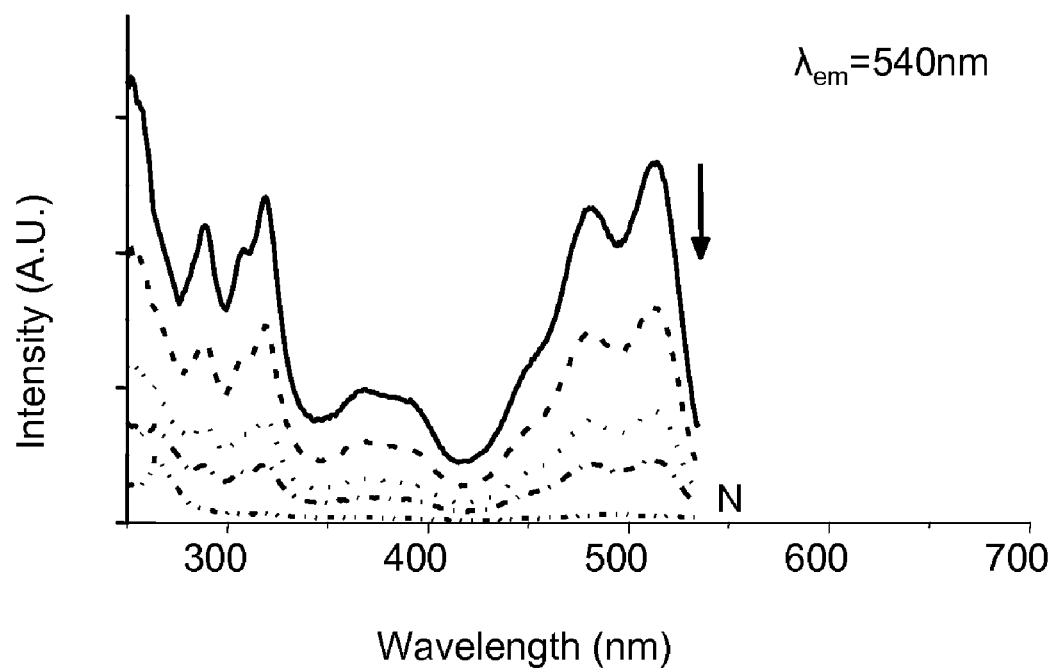
Figure 1D:
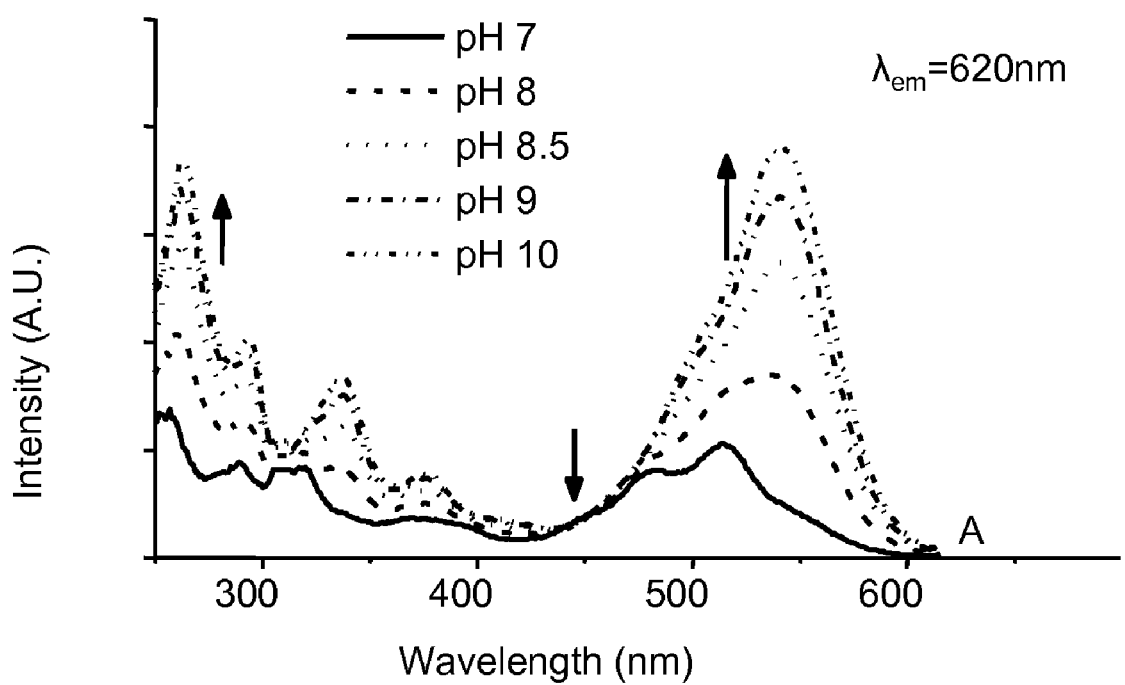

FIGS. 1A through 1H depict the spectral properties of 30 µM SNAFR-2 in 50 mM phosphate buffer with 0.25% DMSO at various pH values. The arrows indicate the spectral changes as the pH increased in order: 7, 8, 8.5, 9 and 10. A=anionic form. N=neutral form. FIG. 1A depicts Absorption spectra. The * indicates the positions of isosbestic points. FIGS. 1B-D depict excitation spectra, with emission monitored at 400 nm, 540 nm, and 620 nm respectively. FIGS. 1E-H depict emission spectra with excitations at 325 nm, 488 nm, 514 nm, and 543 nm respectively, wavelengths that correspond to common laser lines. All fluorescence spectra were normalized versus the maximum for each data set.

Figure 1E:
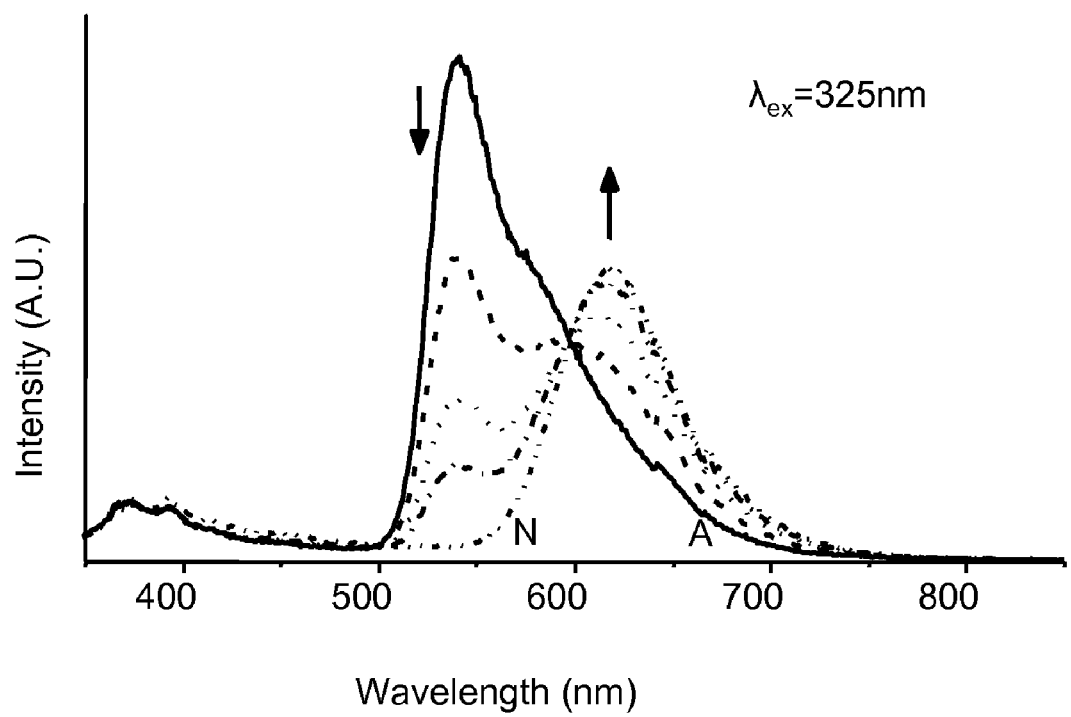
Figure 1F:
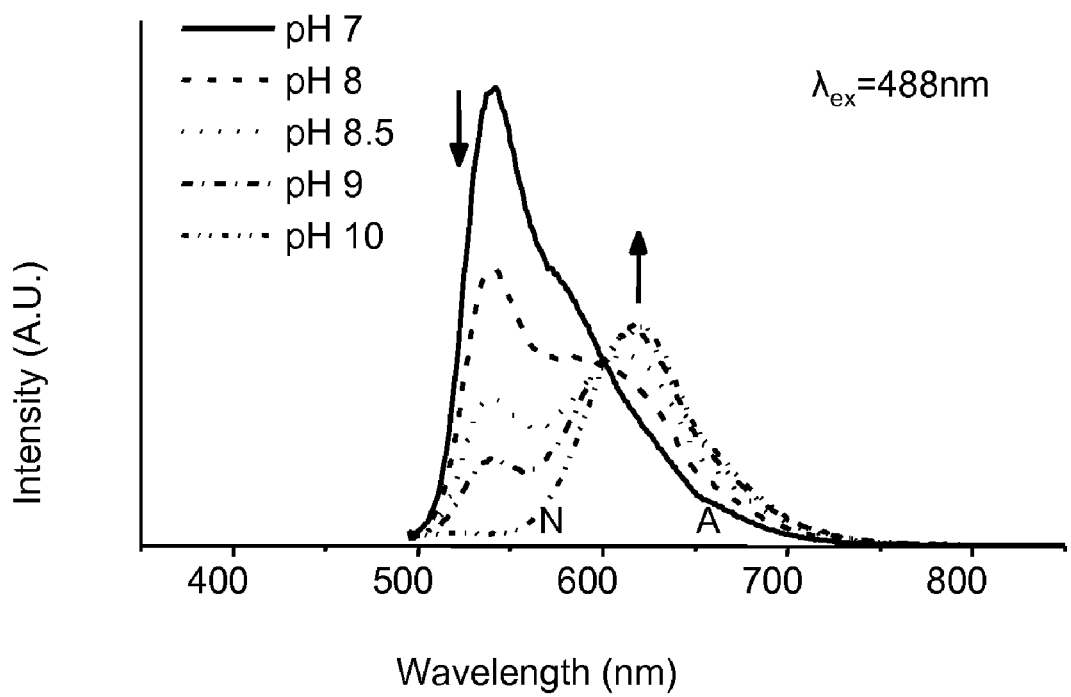
Figure 1G:
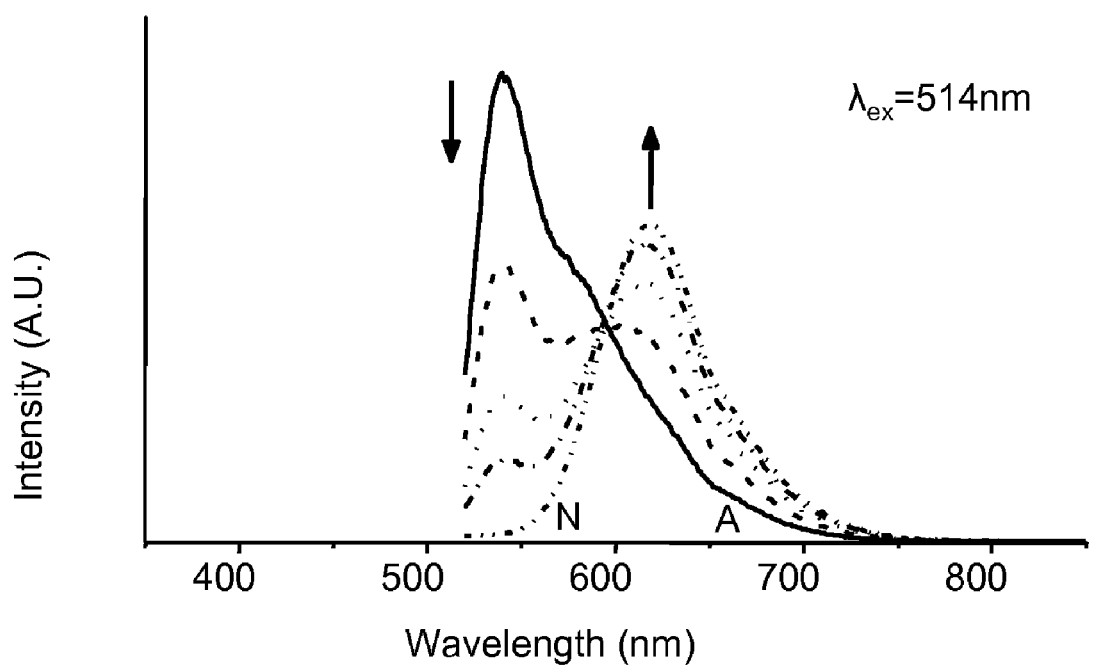
Figure 1H:
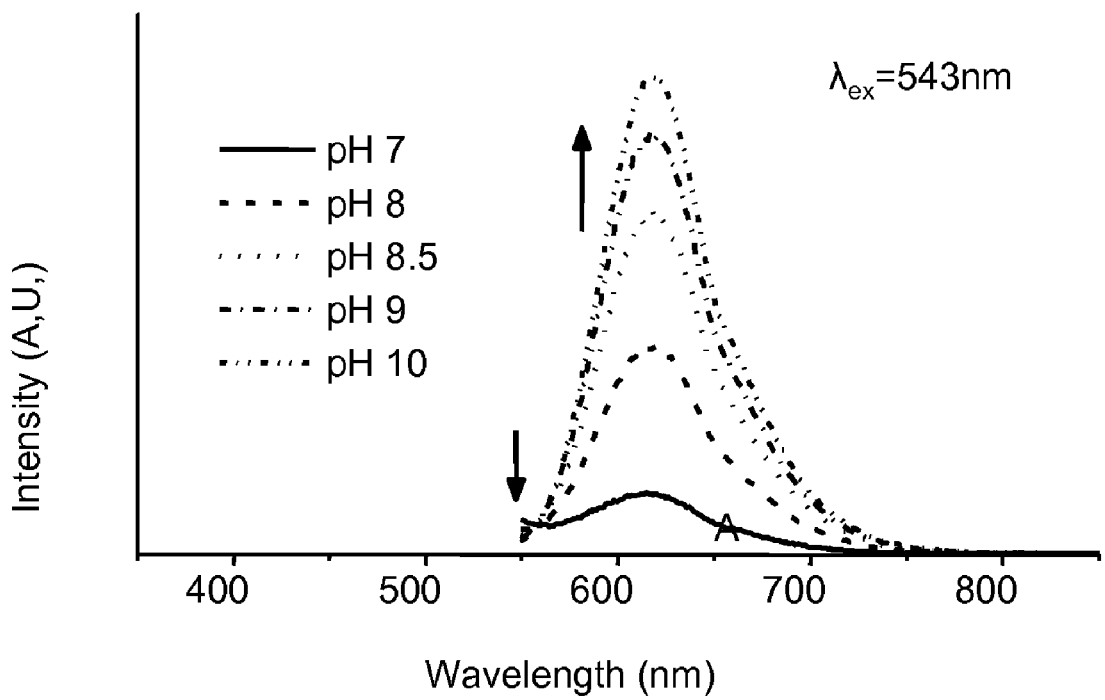

As solution pH increased, the intensity of the red emission band (620 nm), corresponding to the anionic form (A), increased; while that of the green emission band (540 nm), corresponding to the neutral (N) form, decreased (FIGS. 1E-H). The two emission bands were well separated, and showed clear isoemissive points ~600 nm when the molecules were excited at 325, 488, or 514 nm (FIGS. 1E-G). However, with excitation at 543 nm, only the tail of the emission from the neutral form, and emission from the anion were observed. A clear isoemissive point was seen at 560 nm (FIG. 1H). Excitation at longer wavelengths further reduced emission from the neutral form, and eventually led to red emission from the anion form only, with no isoemissive point.

Most prior organic fluorophores have been limited by a narrow excitation range, which has hindered their use in multiplexing systems with other fluorophores. By contrast, the absorption and excitation spectra of SNAFR-2 allow it to be excited from 260 nm to 600, a range that includes various common laser lines, for example, HeCd at 325 nm, Ar ion at 488 and 514 nm, and HeNe at 543 nm (FIGS. 1A-D). SNAFR-2 is compatible with commercially available filter sets, such as those used in various spectroscopic instruments and fluorescence microscopes. The $pK_a$ values for SNAFR-2 inferred from absorption and emission data are summarized in Table 2. The $pK_a$ values inferred from emission spectra using different excitation wavelengths varied from 8.31 to 8.38, with an average $pK_{a\text{-}em}$ of 8.34±0.02. The $pK_a$ values calculated from absorption spectra based on different isosbestic points varied from 8.47 to 8.68, with an average $pK_{a\text{-}abs}$ of 8.53±0.06. The difference between the $pk_{a\text{-}abs}$ values and $pK_{a\text{-}em}$ values suggested the occurrence of excited-state proton transfer. Following excitation, the acidity of SNAFR-2 apparently increased, as measured in phosphate buffer with 0.25% DMSO. The $pK^*_a$ values for SNAFR-2 estimated using the Forster equation are summarized in Table 3. When different methods were used to calculate the frequency of light needed to excite the molecule from its ground state to its lowest excited state, the $pK^*_a$ value was found to vary from 3.3 to 6.3. When the 0-0 excitation method was used, $\tilde{v}_{anion} - \tilde{v}_{neutral}$ was found to be 1813 $cm^{-1}$. The $pK^*_a$ was calculated as 4.54 or 4.73 at room temperature, determined as $pK_{a\text{-}em}$ and $pK_{a\text{-}abs}$, respectively. These results demonstrated that the acidity of SNAFR-2 increased in the excited state.

TABLE 2

$$pH = pK_a + c\left[\log\frac{R - R_{min}}{R_{max} - R}\right] + \log\frac{I^a}{I^b}$$

| Method | $\lambda_{ex}$ | $\lambda_{isobestic}$ | $\lambda_1/\lambda_2$ | $R_{max}$ | $R_{min}$ | $pK_a$ |
|---|---|---|---|---|---|---|
| Em | 325 | — | 627/597 | 1.33 | 0.54 | 8.38 |
| Em | 325 | — | 575/597 | 1.42 | 0.35 | 8.32 |
| Em | 325 | — | 541/597 | 2.31 | 0.06 | 8.32 |
| Em | 488 | — | 630/600 | 1.16 | 0.51 | 8.35 |
| Em | 488 | — | 575/600 | 1.47 | 0.32 | 8.36 |
| Em | 488 | — | 542/600 | 2.47 | 0.05 | 8.33 |
| Em | 514 | — | 623/595 | 1.44 | 0.57 | 8.34 |
| Em | 514 | — | 575/595 | 1.33 | 0.36 | 8.32 |
| Em | 514 | — | 539/595 | 2.16 | 0.02 | 8.31 |
| Abs | — | 484 | 543/484 | 3.76 | 0.88 | 8.52 |
| Abs | — | 484 | 511/484 | 2.04 | 1.23 | 8.54 |
| Abs | — | 484 | 469/484 | 0.48 | 0.37 | 8.47 |
| Abs | — | 394 | 380/394 | 1.41 | 1.14 | 8.68 |
| Abs | — | 394 | 344/394 | 2.73 | 1.90 | 8.58 |
| Abs | — | 327 | 380/327 | 0.52 | 0.40 | 8.51 |
| Abs | — | 327 | 344/327 | 0.99 | 0.67 | 8.51 |
| Abs | — | 327 | 312/327 | 1.17 | 0.99 | 8.54 |
| Abs | — | 304 | 312/304 | 0.91 | 0.75 | 8.48 |
| Abs | — | 304 | 296/304 | 1.38 | 1.13 | 8.54 |
| Abs | — | 304 | 265/304 | 2.79 | 2.07 | 8.48 |

Table 2. The $pK_a$ of SNAFR-2 in 50 mM phosphate buffer was determined using the equation shown in the table (see J. Whitaker et al., Anal. Biochem. 1991, 194, 330-344.). The $pK_a$ was taken as the intercept of the plot of pH versus the first log term in the equation; where c is the slope; R is the ratio from the spectra data at $\lambda_1$ and $\lambda_2$; $R_{max}$ and $R_{min}$ are the limiting values of this ratio; and $I^a/I^b$ is the ratio of the spectral intensity in acid to that in base at the wavelength chosen for the denominator of R. This last term may be neglected by choosing an isosbestic or isoemissive point.

TABLE 3

$$pK_a^* = pK_a - \frac{N_A hc(\tilde{v}_{anion} - \tilde{v}_{neutral})}{2.303RT}$$

| | Neutral form | | | Anionic form | | | | |
|---|---|---|---|---|---|---|---|---|
| Methods | $\tilde{v}_{neutral}$ | $\lambda_{neutral}$ | Methods | $\tilde{v}_{anion}$ | $\lambda_{anionl}$ | $\tilde{v}_{anion} - \tilde{v}_{neutral}$ | $pK_a^{-em^*}$ | $pK_a^{-abs^*}$ |
| Absorption | 19495 | 512.94 | Absorption | 18451 | 541.99 | 1045 | 6.15 | 6.34 |
| Excitation | 19608 | 510.00 | Excitation | 18519 | 540.00 | 1089 | 6.05 | 6.25 |
| Emission | 18484 | 541.00 | Emission | 16103 | 621.00 | 2381 | 3.34 | 3.54 |
| 0-0 absorption[a] | 18789 | 532.23 | 0-0 absorption | 17248 | 579.77 | 1541 | 5.11 | 5.30 |
| 0-0 excitation[a] | 19084 | 524.00 | 0-0 excitation | 17271 | 579.00 | 1813 | 4.54 | 4.73 |

[a] 0-0 absorption/excitation is the intersection of the emission with absorption/excitation spectra of neutral or anionic form, respectively.

White Light Fluorescence

Example 33

SNAFR-2 Is a Single-Component, Red-Green-Blue (RGB) Fluorophore

A third emission band was also seen for the SNAFR-2 molecule at 390 nm following UV excitation (FIGS. 1B, E). SNAFR-2 emitted in each of three separate spectral regions: violet-blue ($\lambda_{em}$=390 nm), green ($\lambda_{em}$=540 nm), and red ($\lambda_{em}$=620 nm). The violet-blue emission was of relatively low intensity compared to the other two. However, the intensity of the blue emission increased in organic solvents. The existence of any blue emission at all was highly unexpected.

Spectral Properties of SNAFR-2 in Organic Solvents

Example 34

Spectral Properties of SNAFR-2 in MeOH

SNAFR-2 exhibited dual emission in organic solvents such as MeOH and DMSO, with emission bands at 390 and 560 nm in DMSO, and 385 and 550 nm in MeOH. Spectral properties of SNAFR-2 in DMSO and MeOH are summarized in Table 4. The violet-blue emission increased in these organic solvents as compared to buffer. The green emission was attributed to the neutral form. As expected, the emission corresponding to the anionic form decreased in both solvents.

TABLE 4

| | DMSO | MeOH |
|---|---|---|
| $\lambda_{abs}^{a}$ (nm) | 493, 528 | 489, 523 |
| $\epsilon^{b}$ (M$^{-1}$cm$^{-1}$) | 7500, 6000 | 11800, 13200 |
| $\lambda_{em}^{c}$ (nm) | 390, 560 | 385, 550 |
| $\lambda_{em}^{d}$ (nm) | 560 | 550 |
| $\Phi^{e}$ | 0.33 | 0.41 |

[a] $\lambda_{abs}$ are peak locations in the absorbance spectra.
[b] $\epsilon$ is the molar extinction coefficient corresponding to each $\lambda_{abs}$.
[c] $\lambda_{em}$ are the peak locations in the emission spectra with excitation at 325 nm.
[d] $\lambda_{em}$ are peak locations in the emission spectra with excitation at 488 nm and 514 nm.
[e] Quantum yields of compound SNAFR-2 relative to rhodamine 6G in EtOH ($\Phi$ = 1). The excitation wavelength was 514 nm for both SNAFR-2 and rhodamine 6G.

When a small amount of phosphate buffer (0.25% final volume) was added to the DMSO solution of SNAFR-2, a third emission band appeared, a deep red. This emission band, attributed to the anionic form, appeared to correspond with a decrease in intensity of the green emission (neutral). The three emission bands had nearly equal intensities in the violet-blue, green, and red regions upon UV excitation when a small amount of neutral buffer was present in the organic solvent. As a result, the emission appeared nearly white to the human eye. SNAFR-2 can be excited over a 400 nm spectral window, between ~260 nm and ~660 nm, with emissions of violet, yellow, green, deep red, and white.

Example 35

Spectral Properties of SNAFR-2 in DMSO

Figure 2A:
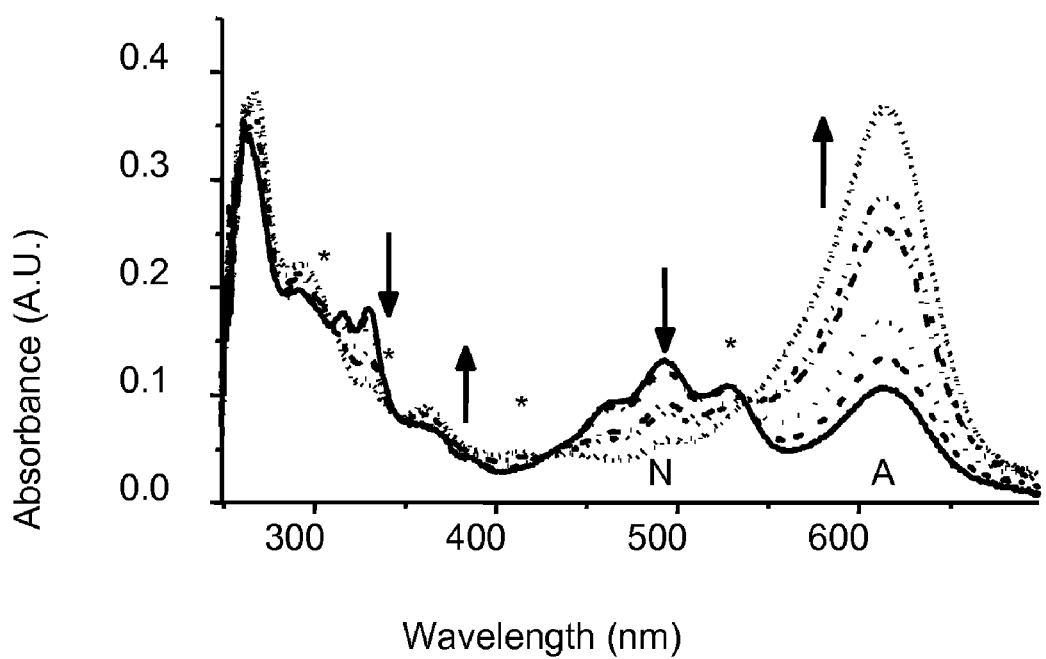
Figure 2B:
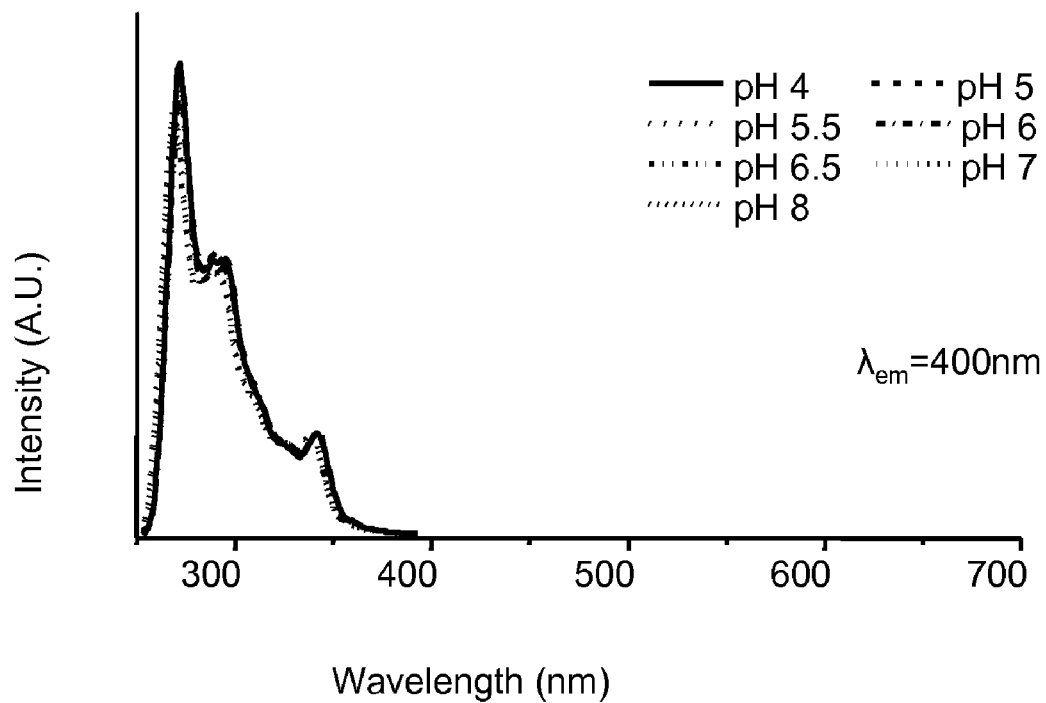
Figure 2C:
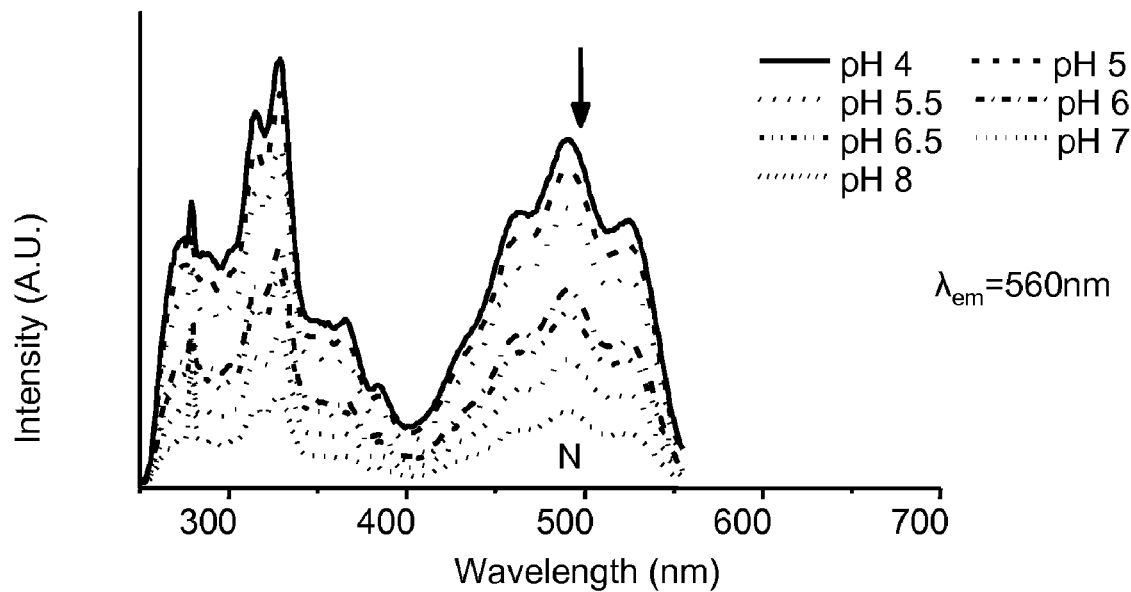
Figure 2D:
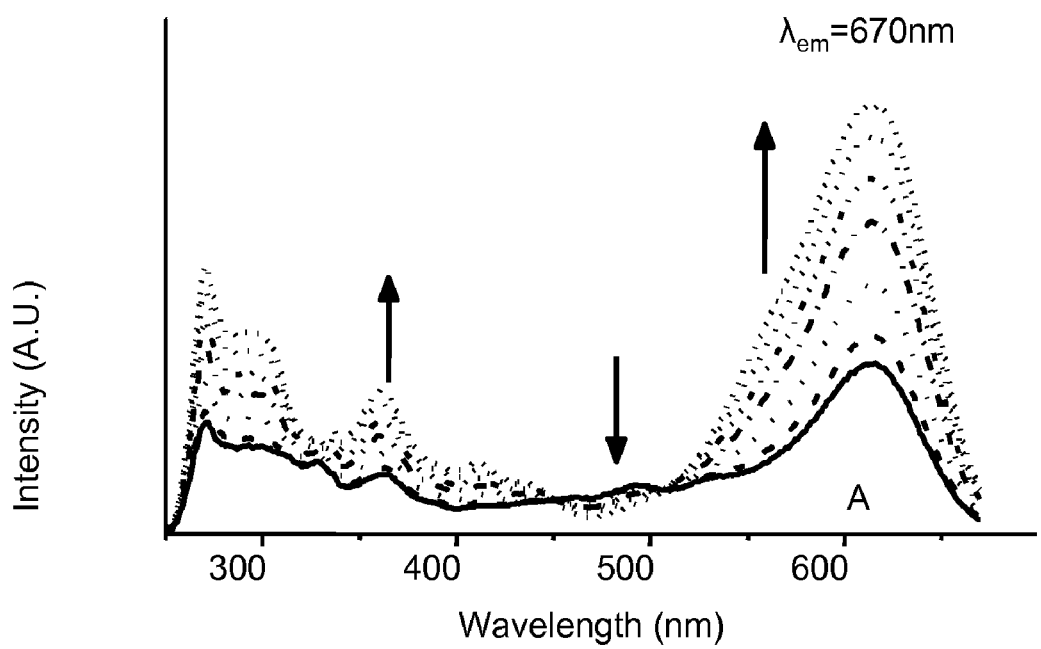

FIGS. 2A through 2I depict the absorption and fluorescence spectra of as a function of phosphate buffer pH. Spectra were measured for 30 μM SNAFR-2 in 50 mM phosphate buffer at various pH values, with 0.25% DMSO. The arrows indicate the spectral changes as the pH increased in order: 4, 5, 5.5, 6, 6.5, 7, and 8. A=anionic form. N=neutral form. FIG. 2A depicts absorption spectra; the * indicates the position of isosbestic points. FIGS. 2B through 2D depict excitation spectra with emission monitored at 400 nm, 560 nm, and 670 nm respectively. FIGS. 2E through 2I depict emission spectra with excitations at 325 nm, 488 nm, 514 nm, 543 nm, and 633 nm, respectively, all of which correspond to common laser lines. All fluorescence spectra were normalized versus the maximum of each data set.

Figure 2E:
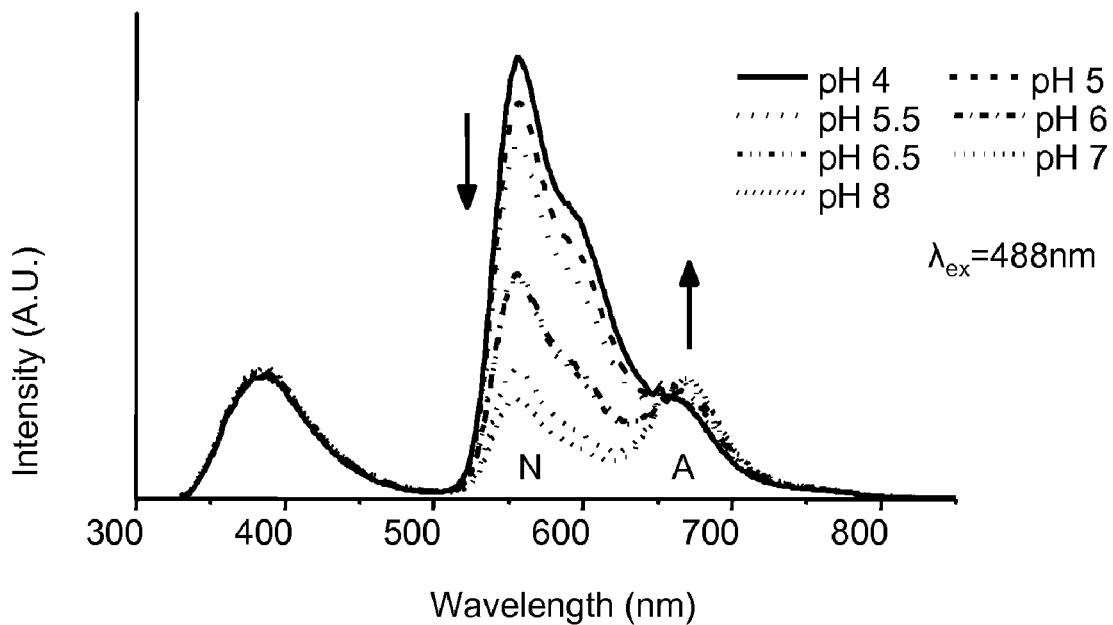

When the buffer pH was low, absorption peaks from the neutral and anionic forms were distinct. Above pH ~6, absorption from the anion form dominated. Four clear isosbestic points were observed: at 311, 345, 427, and 538 nm (FIG. 2A). In emission spectra from excitations at wavelengths shorter than the 538 nm isosbestic point, the green (neutral) emission at 560 nm decreased with increasing buffer pH. The opposite was seen for the red (anionic) emission at 670 nm (FIGS. 2E-I). As seen in FIG. 2I, excitation at 633 nm, much longer than the 538 nm isosbestic point, excited only the anion, yielding only the emission centered at 670 nm, with no isoemissive point.

Figure 2F:
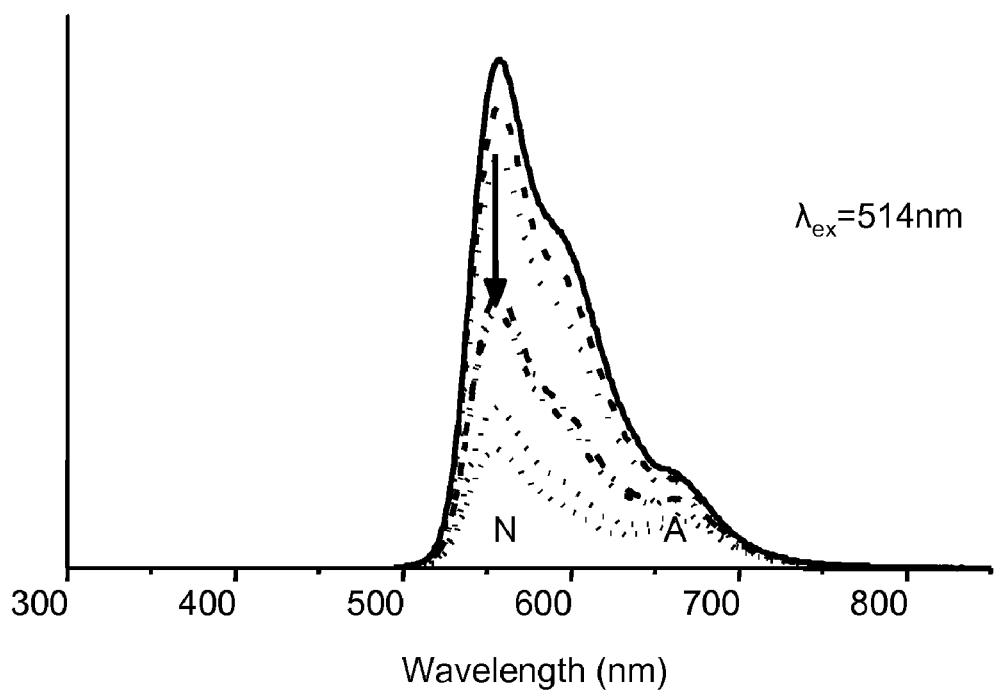
Figure 2G:
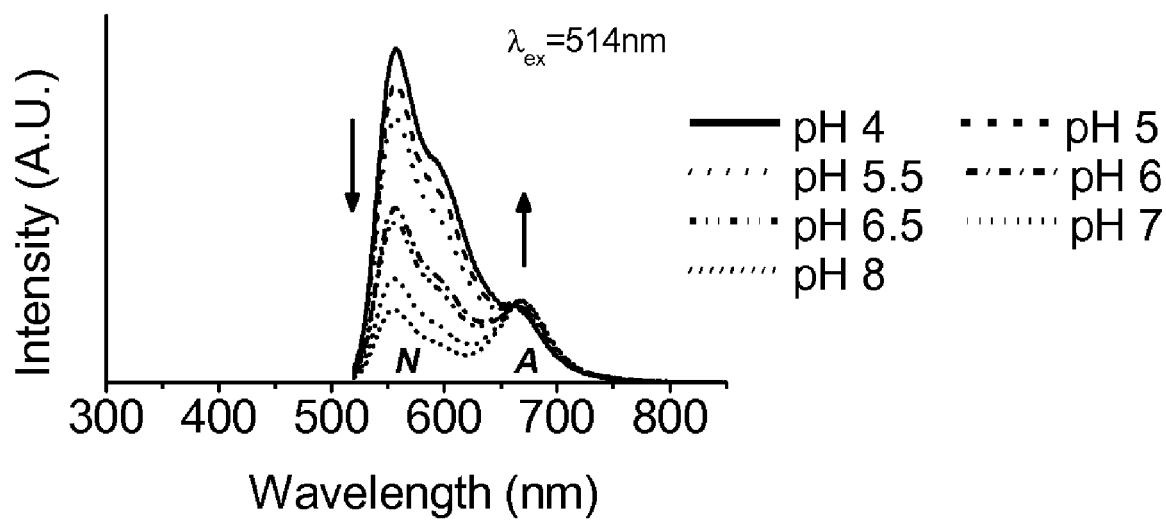

As seen in FIG. 2F, emission from 488 nm excitation had no clear isoemissive point, presumably due to minimal emission from the anion. Under these conditions, emission from the neutral form dominated at all pH values tested.

Figure 2H:
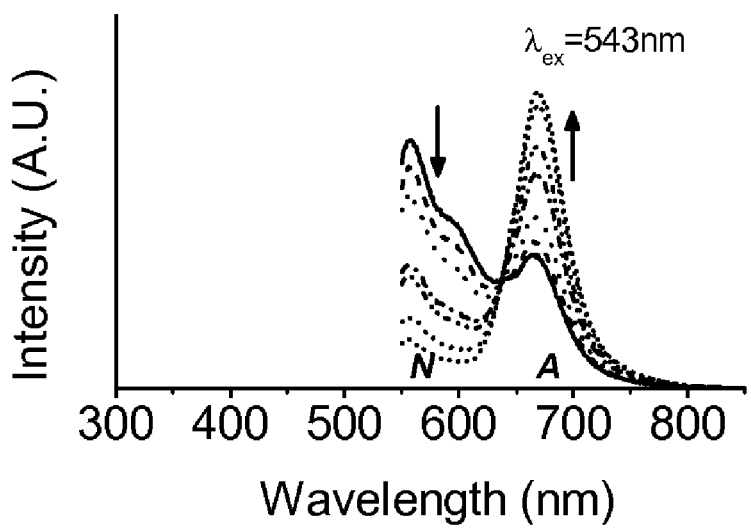
Figure 2I:
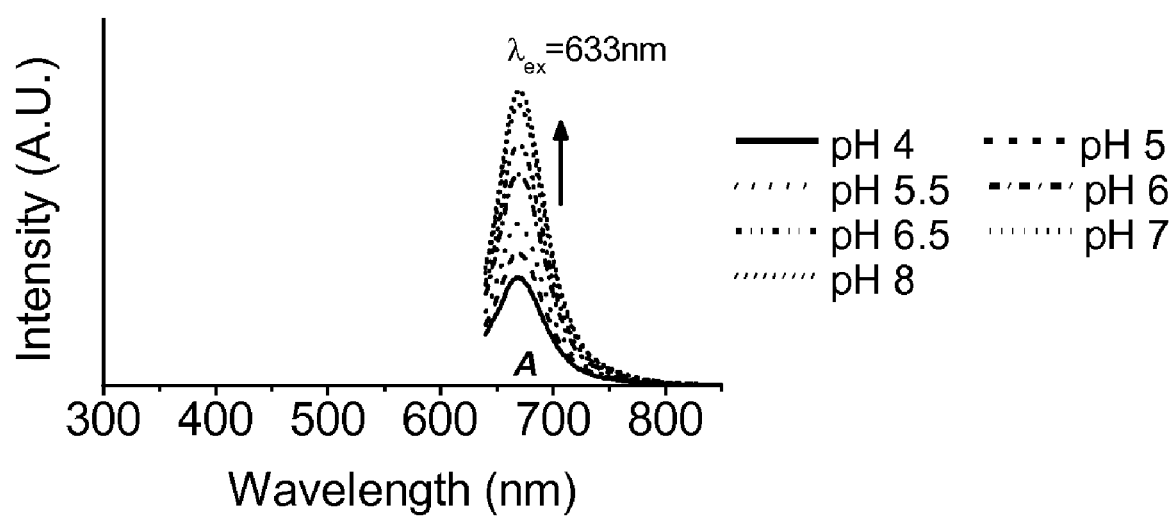

A preferred excitation wavelength for ratiometric measurements is the isosbestic point at 538 nm. The width of this peak readily lends itself to excitation by the 543 nm output of a green HeNe laser (FIG. 2H).

Green fluorescence emission, measured at 560 nm with 490 nm excitation, increased as pH decreased (FIG. 2C). This was attributed to increased levels of the neutral form at low pH. The opposite was observed for red emission at 610 nm, attributed to the anion form (FIG. 2D). The response of SNAFR-2 to pH was similar both in 0.25% DMSO in buffer (FIG. 1), and in 0.25% buffer in DMSO (FIG. 2). This similarity was attributed to the affinity of SNAFR-2 for water, and the resulting preferential solvation of SNAFR-2 by water, even in water-poor DMSO solutions.

In contrast to the red and green emissions, the violet-blue emission did not show strong dependence on buffer pH (FIGS. 2E and 2B).

Example 36

The Chromaticity of SNAFR-2 Emission, and its Sensitivity to Excitation Wavelength and pH Chromaticity coordinates x, y, and z were found by calculating the fractional components of tristimulus values as: x=X/(X+Y+Z), y=Y/(X+Y+Z), z=Z/(X+Y+Z). A "tristimulus" value is the level of one of the three primary colors that specifies a color stimulus. The 1931 CIE (Commission Internationale de L'Eclairage) tristimulus values are denoted as X, Y, and Z. See, e.g., G. Wyszecki, "Colorimetry," pp. 1-15 in W. Driscoll et al. (Eds.) *Handbook of Optics* (1978). All possible sets of tristimulus values can be represented in a two-dimensional plot of two of the three chromaticity coordinates (because by definition x+y+z=1); by convention x and y are generally used. A plot of this type is referred to as a chromaticity diagram; see hyperphysics.phy-astr.gsu.edu/hbase/vision/cie.html#c2; see also colourware.co.uk.

The emission colors may be varied by changing the excitation wavelength or the buffer pH. Excitation between ~270 and ~340 nm produces three emission bands of varying intensities, which can vary in appearance from violet to near-white. With excitation between ~340 and ~415 nm, the emission color appeared yellow, with the disappearance of the violet-blue emission and an increase in green emission. With excitation between ~415 and ~545 nm, SNAFR-2 had stronger green emission, and comparatively weak red emission. At longer excitation wavelengths, ~545 nm to ~650 nm, SNAFR-2 exhibited red emission.

As shown in FIG. 2, green and red emission were pH-dependent, while blue emission was essentially pH-independent. Thus the apparent color of the emission changed significantly as a function of buffer pH. The chromaticity of emission as a function of pH and excitation wavelength from 270 to 340 nm is summarized in Table 3. (Additional table entries may be seen in the Supporting Information for Yang et al., *J. Am. Chem. Soc.*, 2006, 128, 14081-14092, found at pubs.acs.org, the entire disclosure of which is incorporated by reference.)

Figure 3A:
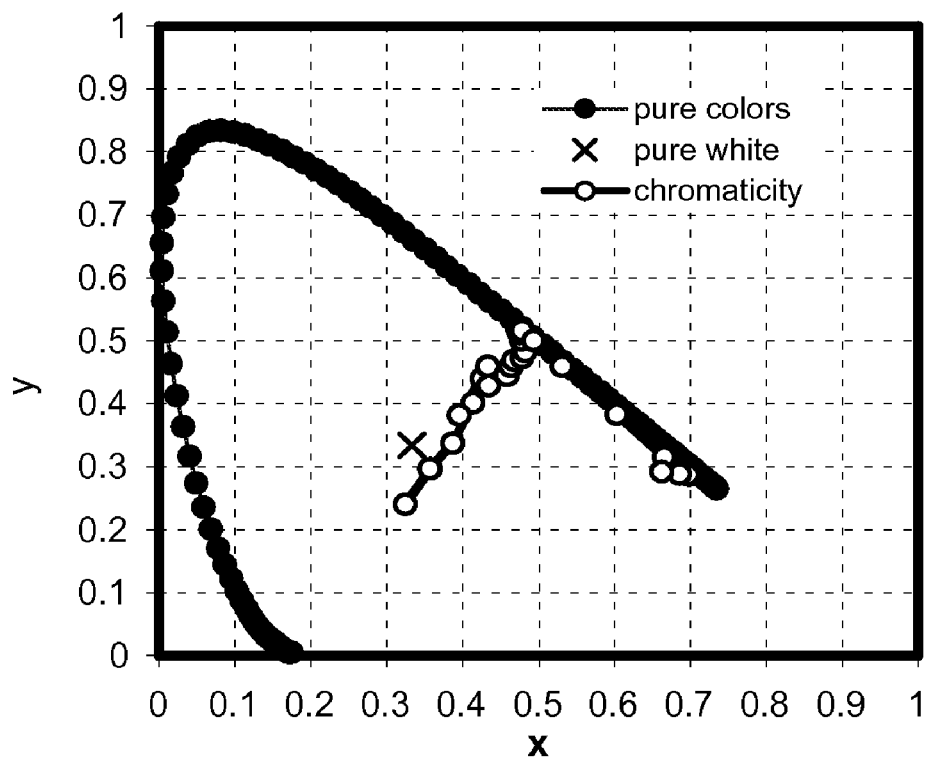
FIG. 3A depicts chromaticity coordinates for 30 μM SNAFR-2 in DMSO with 0.25% phosphate buffer (50 mM, pH 7).
Figure 3B:
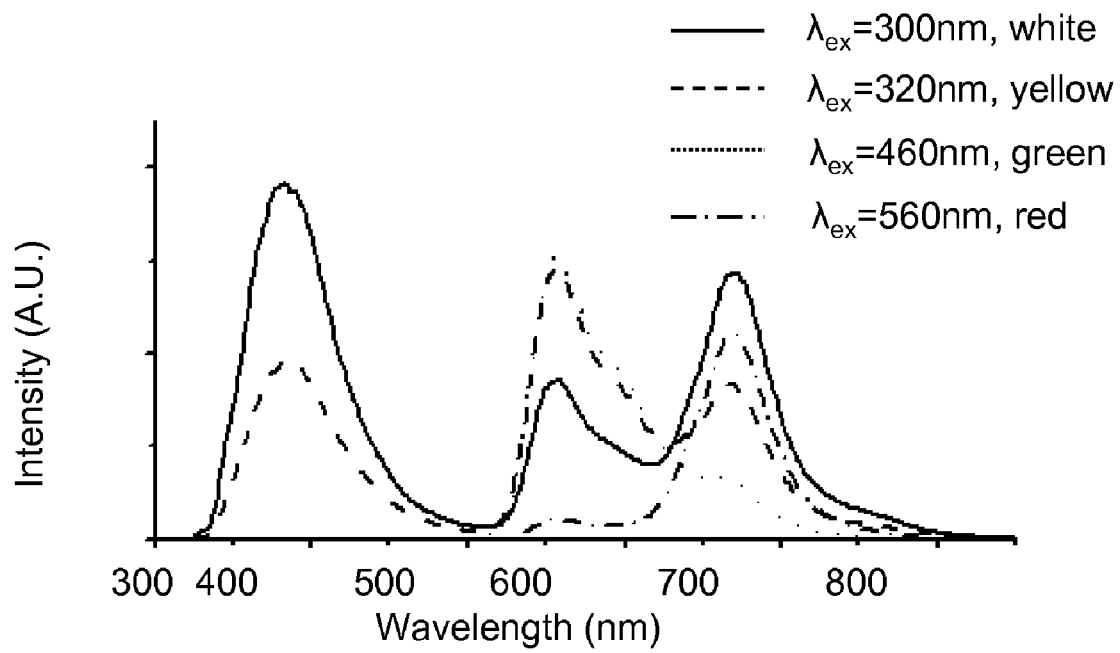
FIG. 3B depicts emission spectra for SNAFR-2 in DMSO with 0.25% PHOSPHATE BUFFER (50 μM, pH 7) when excited at 300, 320, 460 and 560 nm.

FIG. 3A depicts chromaticity coordinates for emission spectra collected with excitation wavelengths between 270 and 650 nm, plotted as a 1931 CIE chromaticity diagram, for a solution of 30 µM SNAFR-2 in DMSO with 0.25% phosphate buffer (50 mM, pH 7). FIG. 3B depicts emission spectra for SNAFR-2 in DMSO with 0.25% phosphate buffer (50 µM, pH 7), with excitations at 300, 320, 460 and 560 nm, respectively, producing emissions appearing as near-white, yellow, green, and red in color. In both FIGS. 3A and 3B, the arrows indicate the spectral changes as the pH increased in order: 4, 5, 5.5, 6, 6.5, 7, and 8.

Example 37

Mechanism of the Violet-Blue Emission

Figure 8A:
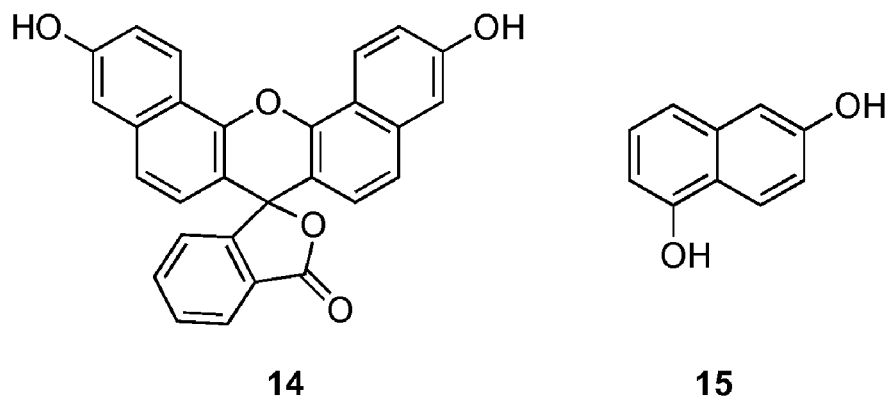
FIG. 8A depicts the structures of Compounds 14 and 15.
Figure 8B:
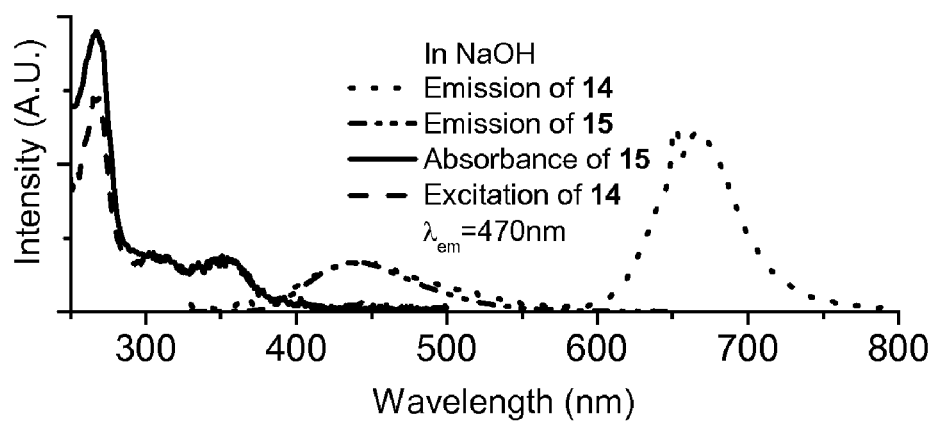
FIG. 8B depicts emission spectra of Compounds 14 and 15 in NaOH, excited at 325 nm, monitored at 470 nm.
Figure 8C:
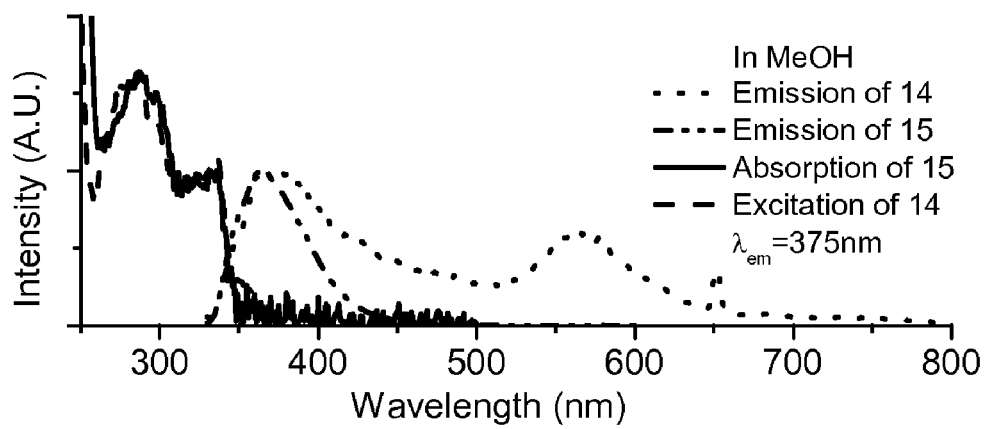
FIG. 8C depicts emission spectra of Compounds 14 and 15 in MeOH, excited at 325 nm, monitored at 370 nm.

We investigated the mechanism of the violet-blue emission, using benzo[c]-fluorescein Compounds 14 and 15 as model naphthyl-containing fluorophores for comparison. The blue emission of Compound 14 is similar to that of Compound 15 (FIG. 8). Monitoring emission at 470 nm (blue band), the excitation spectrum of Compound 14 was similar to the absorption spectrum of Compound 15 (in 0.1 M NaOH, FIG. 8B). Similar behavior was seen in MeOH (FIG. 8C). These observations support the hypothesis that Compounds 14 and 15 have a similar mechanism of blue emission in both solvents.

We thus hypothesize that the blue emission from SNAFR-2 and Compound 14 both arise from an "isolated" naphthyl moiety; i.e., the molecular bonding becomes such that the naphthyl group is no longer conjugated to other double bonds in the molecule. In Compound 14, the lactone form would isolate the naphthyl fluorophore. In organic solvents, it is known that the lactone form of xanthenes predominates.

FIG. 8B depicts the emission spectra of Compounds 14 and 15 following excitation at 325 nm, together with the excitation spectrum of Compound 14 with emission monitored at 470 nm, and the absorption spectrum of Compound 15. All compounds were in 0.1 M NaOH.

FIG. 8C depicts emission spectra of Compounds 14 and 15 following excitation at 325 nm, the excitation spectrum of Compound 14, with emission monitored at 370 nm, and the absorption spectrum of Compound 15. The concentrations of Compound 14 were 10 µM, and those of Compound 15, 30 µM. All spectra were taken in MeOH solution, and were normalized to facilitate comparison.

In MeOH we observed a more intense emission in the blue than in the green (FIG. 8C). In 0.1 M NaOH solution, equilibrium favored the formation of the carboxylate anion rather than the lactone, leading to a more intense red emission (FIG. 8B). However, the presence of lactone (or of a covalently-attached hydroxide) apparently still induced some blue, naphthyl-derived emission.

Figure 18:
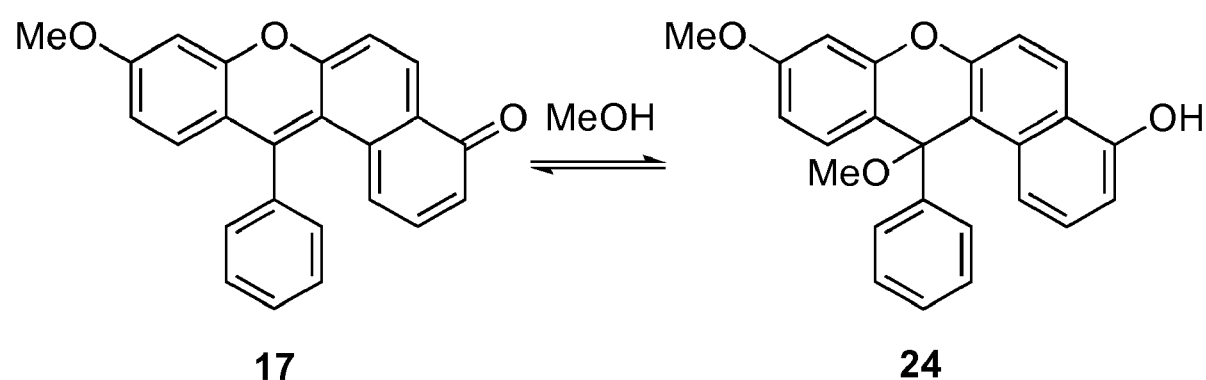
FIG. 18 depicts tautomerization between Compounds 17 and 24.

Although SNAFR-2 has no lactone to isolate the naphthalene fluorophore, its blue emission in various solvents nevertheless resembled those of Compounds 14 and 15. We suggest an alternative mechanism to isolate the naphthalene unit, to account for the violet-blue emission of SNAFR-2. Our experimental evidence showed that intermolecular nucleophilic addition readily occurred in the naphtho[a]- and naphtho[b]-xanthene series. First, compound 16, the isolated adduct possessing a methyl ether at the bridging benzylic carbon, exhibited primarily violet-blue emission (FIG. 1A). Second, Compound 17, the methyl ether analogue of one tautomer of SNAFR-1, also undergoes nucleophilic addition to its central carbon, to produce Compound 24, as depicted in FIG. 18.

Figure 4A:
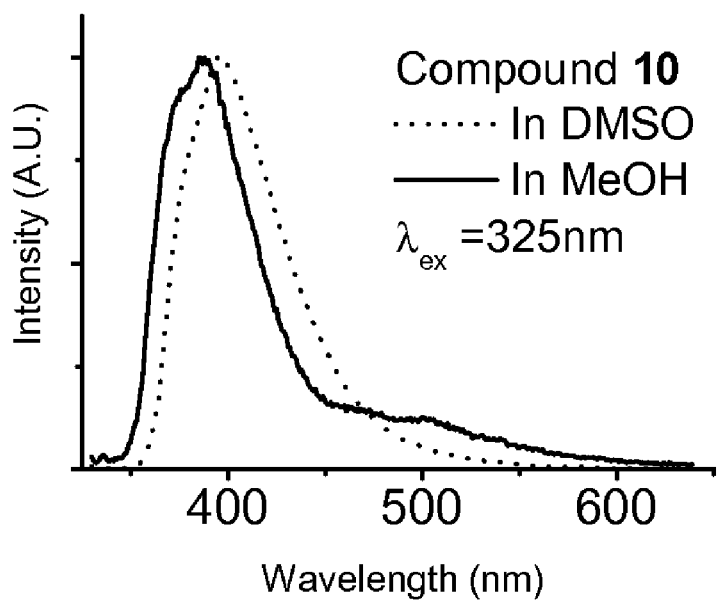
FIG. 4A depicts the fluorescence emission of 30 μM Compound 10 in DMSO and in MeOH.
Figure 4B:
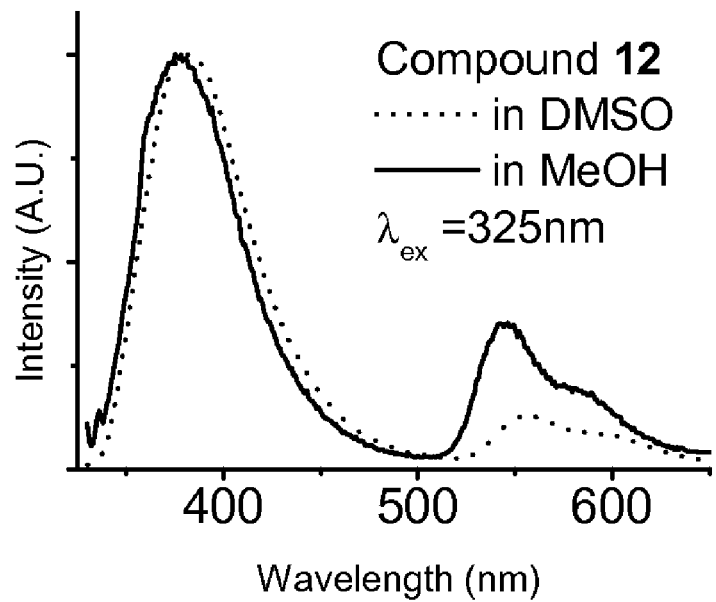
FIG. 4B depicts the fluorescence emission of 25 μM Compound 12 in DMSO and in MeOH.
Figure 4C:
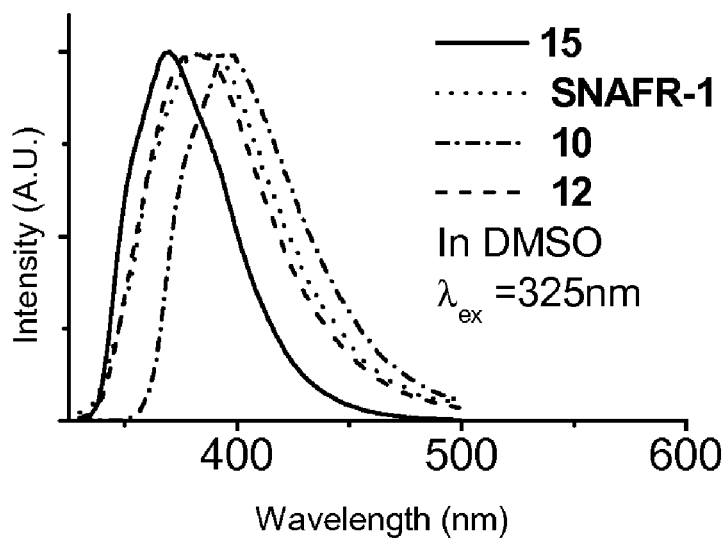
FIG. 4C depicts an overlay of the violet-blue emission of SNAFR-2 with other compounds having an isolated naphthalene moiety, in DMSO.
Figure 4D:
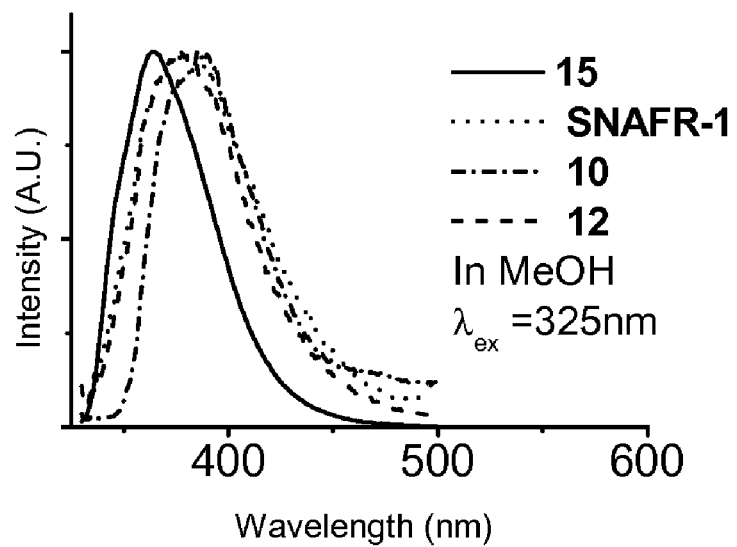
FIG. 4D depicts an overlay of the violet-blue emission of SNAFR-2 with other compounds possessing an isolated naphthalene moiety, in MeOH.
Figure 5:
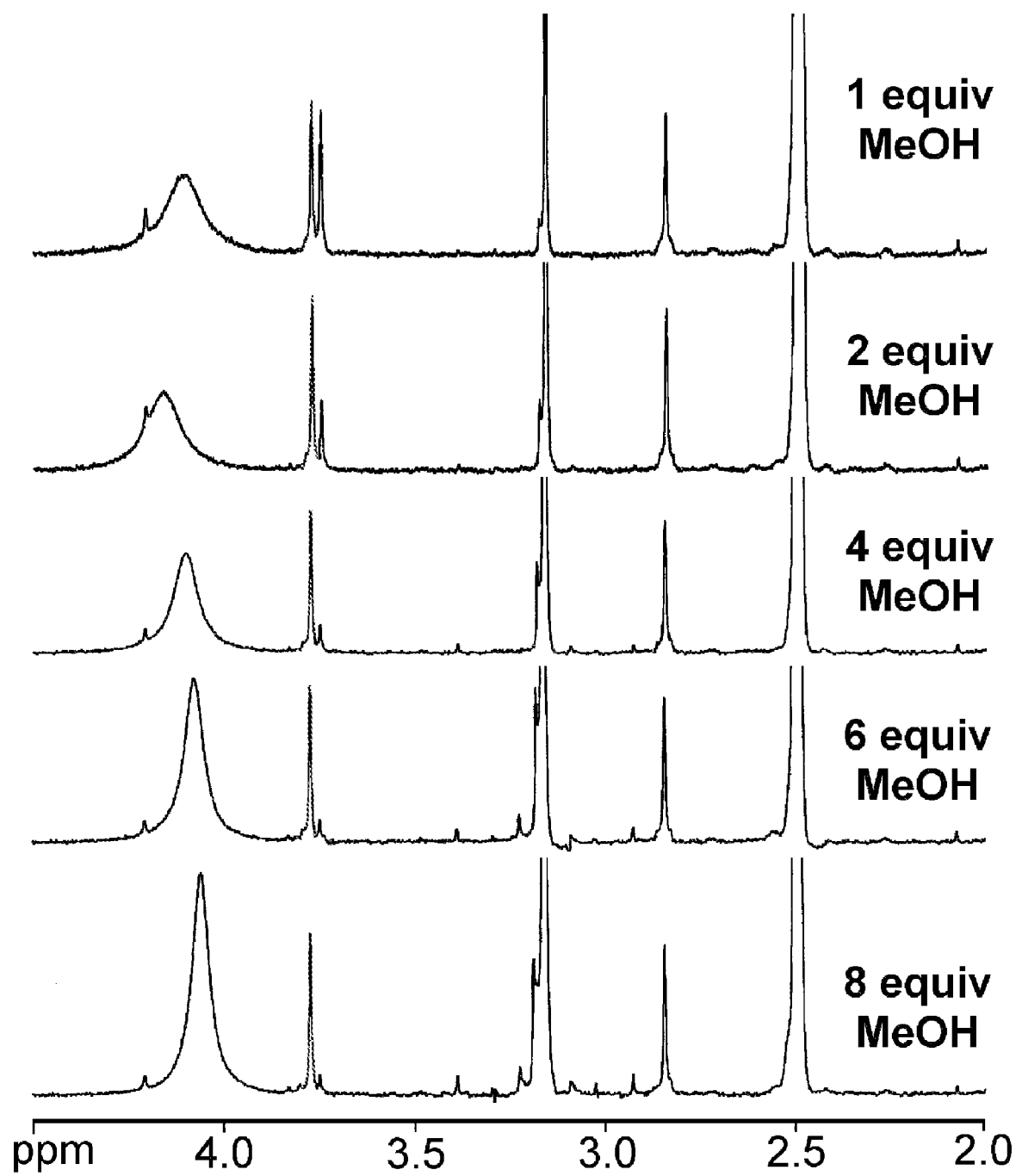
FIG. 5 depicts $^1H$ NMR spectra of the equilibrium between Compounds 17 and 24 in DMSO-$d_6$.

FIG. 5 depicts $^1$H NMR spectra of the equilibrium between Compounds 17 and 24 in DMSO-$d_6$. The concentration of Compound 17 decreased as the MeOH concentration increased. The resonances of the three methyl ether moieties of Compounds 17 and 24 were well-resolved from one another. As the MeOH concentration increased, the relative proportion of Compound 17 decreased. A MeOH solution of Compound 17 displayed an intense blue emission as well as a green emission (FIG. 4B). The red emission of Compound 17 was less than that of tautomerizable SNAFR-2. An overlay of the violet-blue emissions arising from Compounds 15, 16, and 17, and SNAFR-1 and SNAFR-2 in various solvents is shown in FIG. 4. The similar spectral features, along with NMR and single-crystal X-ray structure data were all consistent with our hypothesis that the isolated naphthyl was responsible for the violet-blue emission of this series of compounds. Trace amounts of $H_2O$ in the DMSO apparently acted as a nucleophile. Alternative mechanisms that might also lead to blue emission are also possible, however, such as a local excitation.

FIG. 4A depicts fluorescence emission of Compound 10, 30 μM, in DMSO and MeOH. FIG. 4B depicts fluorescence emission of Compound 12, 25 μM, in DMSO and MeOH. FIG. 4C depicts an overlay of the violet-blue emission of SNAFR-1 with other compounds that have an isolated naphthalene moiety, in each case in DMSO. FIG. 4D depicts an overlay of the violet-blue emission of SNAFR-2 with other compounds that have an isolated naphthalene moiety, in each case in MeOH. All fluorescence spectra were collected using a 325 nm excitation wavelength. The solutions of SNAFR-2 and Compound 15 were 30 μM. All fluorescence spectra were normalized to the maximum of their respective violet-blue peaks.

Example 38

Dual Emission White Light from Compound 17

Figure 6A:
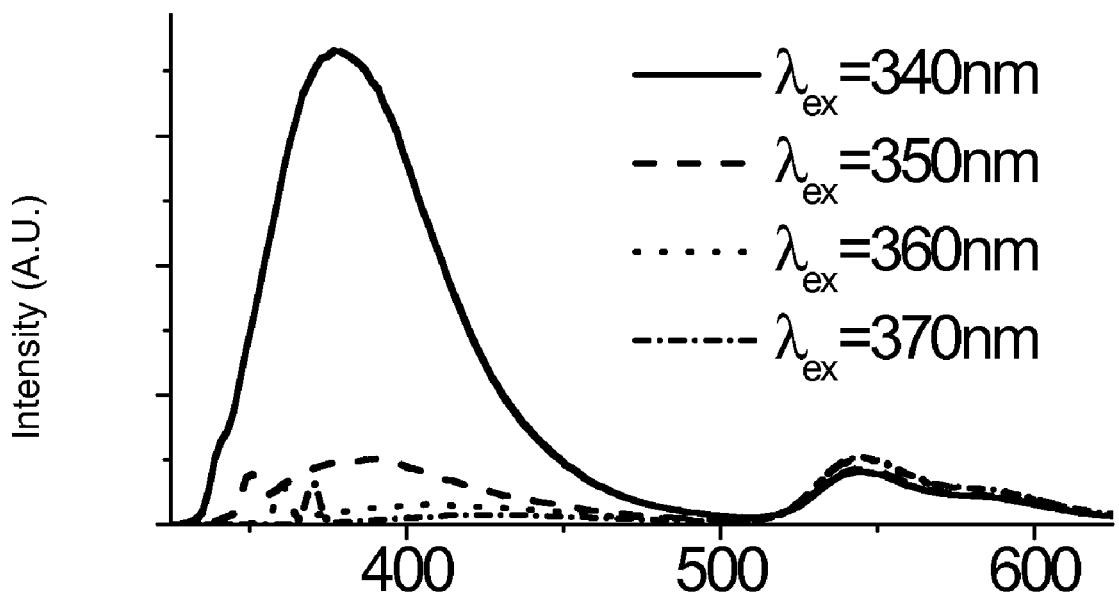
FIG. 6A depicts the emission of 50 μM Compound 12 in MeOH with different excitation wavelengths.
Figure 6B:
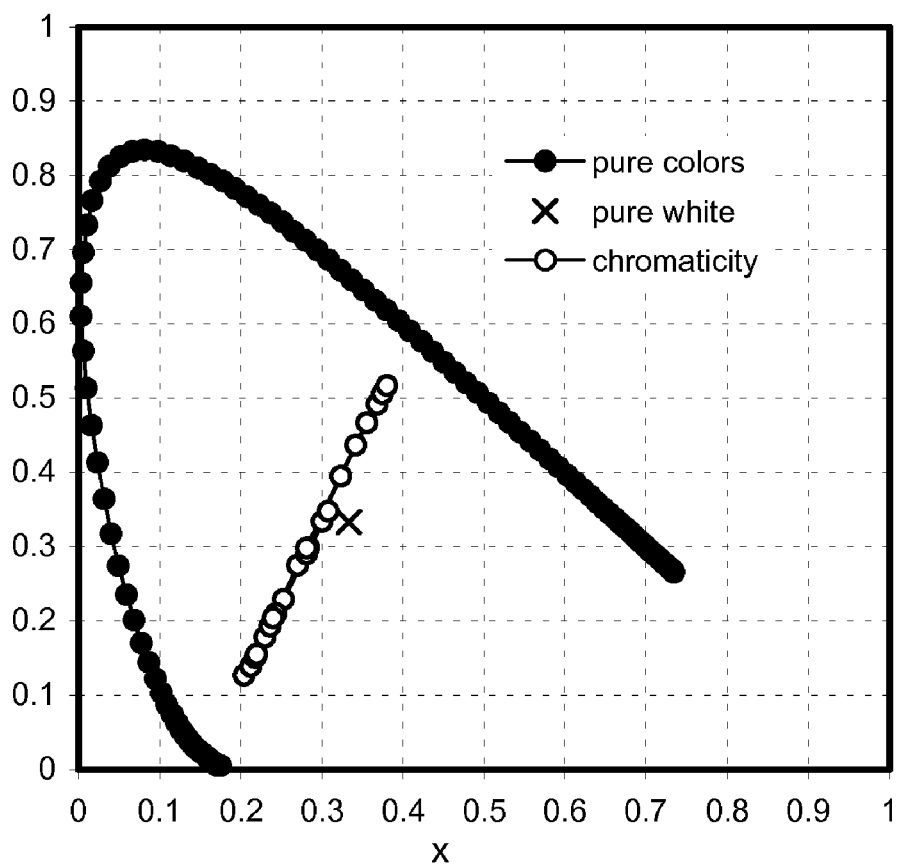
FIG. 6B depicts chromaticity coordinates for emission spectra at excitation wavelengths between 275 and 375 nm.

FIG. 4B depicts dual emission in the violet-blue and in the green from Compound 17 in MeOH. In MeOH only a minimal amount of the Compound 17 tautomer remained in solution, with the majority in the Compound 24 form, leading to a dominant violet-blue emission (~330 to ~450 nm) with a green emission (~520 to 620 nm) when excited below 340 nm. However, as we also saw with SNAFR-1, the relative intensities of these emission bands were dependent on excitation wavelength. FIG. 6A depicts the emission of 50 μM Compound 17 in MeOH. When excited at 350 nm, Compound 17 showed two emission bands of approximately equal intensity. FIG. 6B depicts chromaticity coordinates for emission spectra for a solution of 50 μM Compound 17 in MeOH, at excitation wavelengths between 275 and 375 nm, plotted as a 1931 CIE chromaticity diagram. Excitation at wavelengths below ~340 nm caused the relative intensity of the blue emission band to decrease dramatically, as excitation of the naphthyl unit became less efficient. Following excitation at 350 nm, emission from the two bands was nearly equal, producing a near-white color. Although two-band white light has a poorer color rendering index (CRI) owing to an imbalance in the red color, it is still of interest. Two-band white light is, for example, prevalent in current polymeric white-light emitting diodes.

Example 39

Imaging of Live Cells

Organic fluorophores are widely used in cell imaging. However, they have found only limited use in some sophisticated applications such as multiplexing and real-time measurements. Typical drawbacks of prior fluorophores have been such characteristics as a narrow excitation range, and poor photostability. Relatively few water-soluble, long-wavelength ($\lambda_{em}$>~600 nm), photostable probes have previously been reported. The superior properties of SNAFR-2 and other compounds in accordance with the present invention make them well-suited for cellular imaging. These properties include their multiple emission bands, wide excitation range, low cytotoxicity, and excellent photostability.

Cellular imaging studies showed that SNAFR-2 readily entered HEp2 cells. SNAFR-2 appeared to localize in lipophilic compartments. There was a strong signal from the endoplasmic reticulum, and a smaller signal from mitochondria. The cell nuclei also showed some SNAFR-2 fluorescence, which could be due either to accumulation in the nuclear membrane or to intercalation into DNA. No obvious staining of the plasma membrane was seen. However, since the plasma membrane has a large surface area, a relatively low surface signal might not have been detected. Three different filter sets, DAPI, FITC, and Texas Red, were used to select for wavelengths corresponding to the blue, green, and red emissions of SNAFR-2, respectively. Some autofluorescence from the cell was seen with the DAPI filter. However, autofluorescence was minimal with the longer wavelength filter sets, FITC and Texas Red.

Overnight incubation of HEp-2 cells with SNAFR-2 showed an overall increase in signal intensity as compared to that following a 30 min incubation. There was also a large vesicular formation within the cells, which did not co-localize with the compound's own signal.

Example 40

Photostability of SNAFR-2

We investigated the photostability of SNAFR-2 in MeOH. It proved to be far more photostable than fluorescein in 0.1 M NaOH. In MeOH, SNAFR-2 can be excited efficiently at 488 nm, which corresponds to an Ar ion laser line. This wavelength also matches well with the absorbance maximum ($\lambda_{abs}$=493 nm) of fluorescein in aqueous base.

Figure 9:
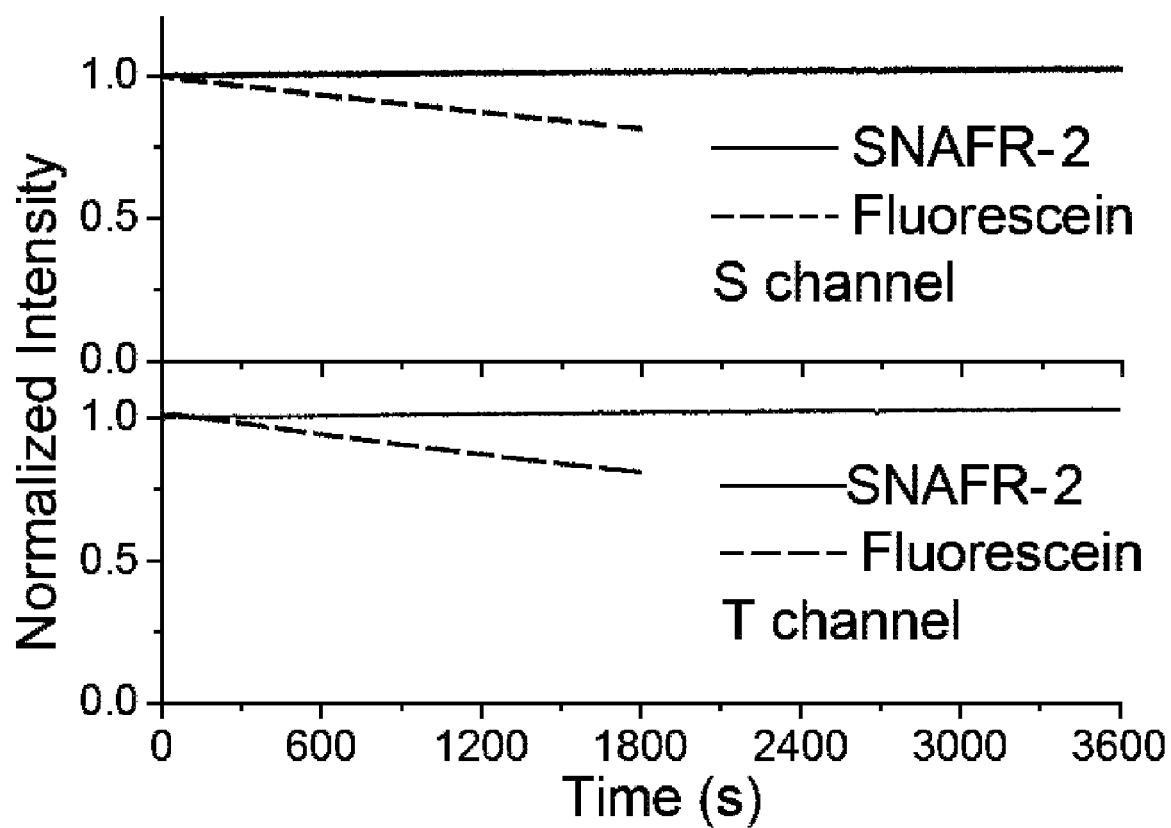
FIG. 9 depicts photobleaching decay of SNAFR-2 in MeOH and of fluorescein in 0.1 M NaOH.
Figure 11:
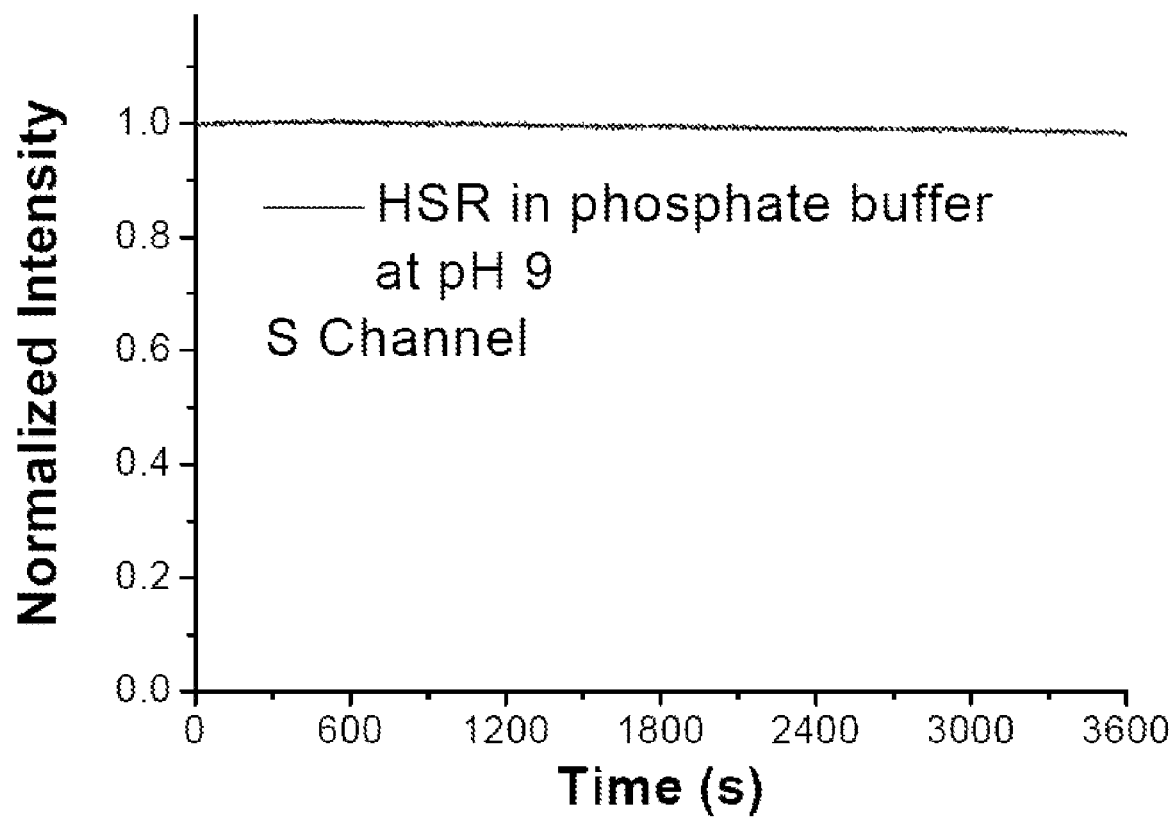
FIG. 11 depicts photobleaching decay of SNAFR-6 in phosphate buffer with 1% DMSO.
Figure 12:
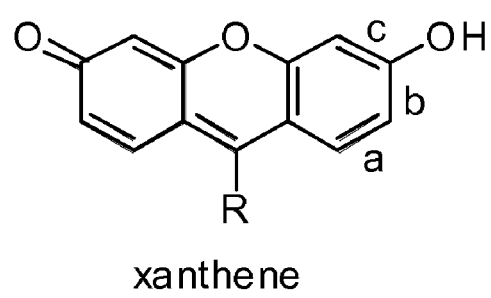
FIG. 12 depicts the structures of xanthene and of three benzoxanthene isomers.
Figure 12:
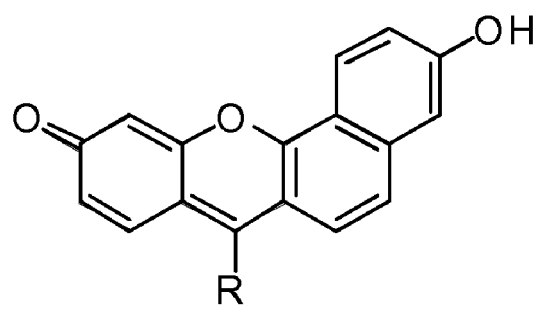
Figure 12:
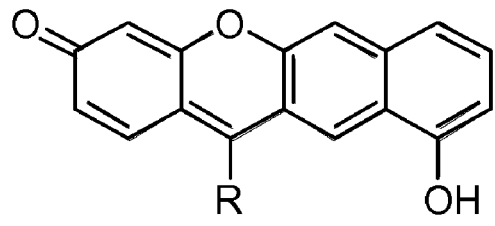
Figure 12:
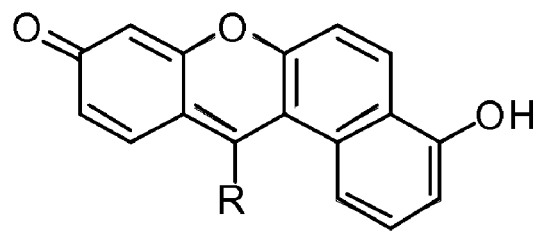
Figure 13:
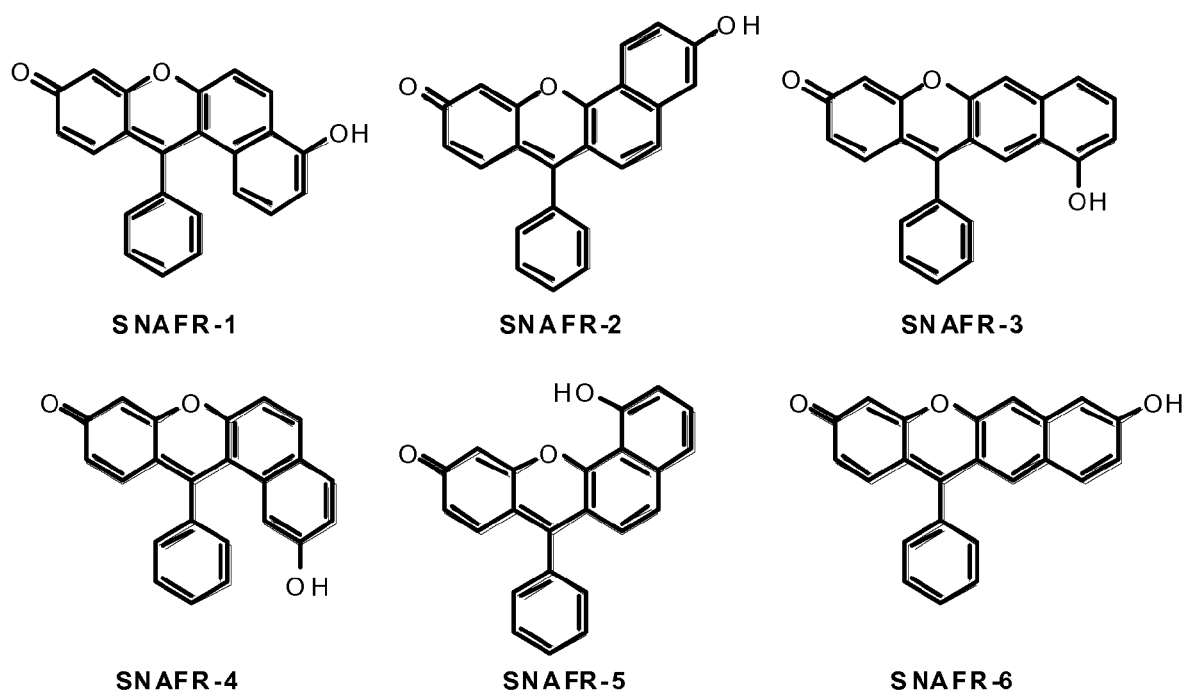
FIG. 13 depicts the structures of the compounds SNAFR-1, SNAFR-2, SNAFR-3, SNAFR-4, SNAFR-5, and SNAFR-6.

We conducted photostability studies in SNAFR-2 and fluorescein solutions, with the concentration of each selected to have an absorbance of 0.03 at 488 nm. The excitation bandpass was opened to 14 nm, the maximum allowed by the instrument we used. The fluorescence signal was collected using both the S- and T-channels of the instrument. S-channel data were collected through a dual monochromator set to the emission maximum of the particular fluorophore. T-channel data were collected through a 550 nm, long-pass filter. High voltage for the photomultiplier tube (PMT) was set to 950 and 500 V for the S and T channels, respectively. Data were collected with a 0.1 s integration time at 0.1 s intervals for at least 1800 s. The signal was maintained within an acceptable range using neutral density filters (Omega Optical, Brattleboro, Vt.). The observed photobleaching decay of each dye is plotted in FIG. 9. SNAFR-2 showed excellent photostability over the time period monitored, while fluorescein lost ~20-30% of its fluorescence after only 30 min. FIG. 11 depicts photobleaching of SNAFR-6 in phosphate buffer with 1% DMSO. Fluorescence intensity was monitored at the emission maximum through a dual monochromator following excitation at 543 nm. Less than 2% bleaching was observed after irradiation for 1 hour.

Example 41

Cytotoxicity of SNAFR-6

Figure 10:
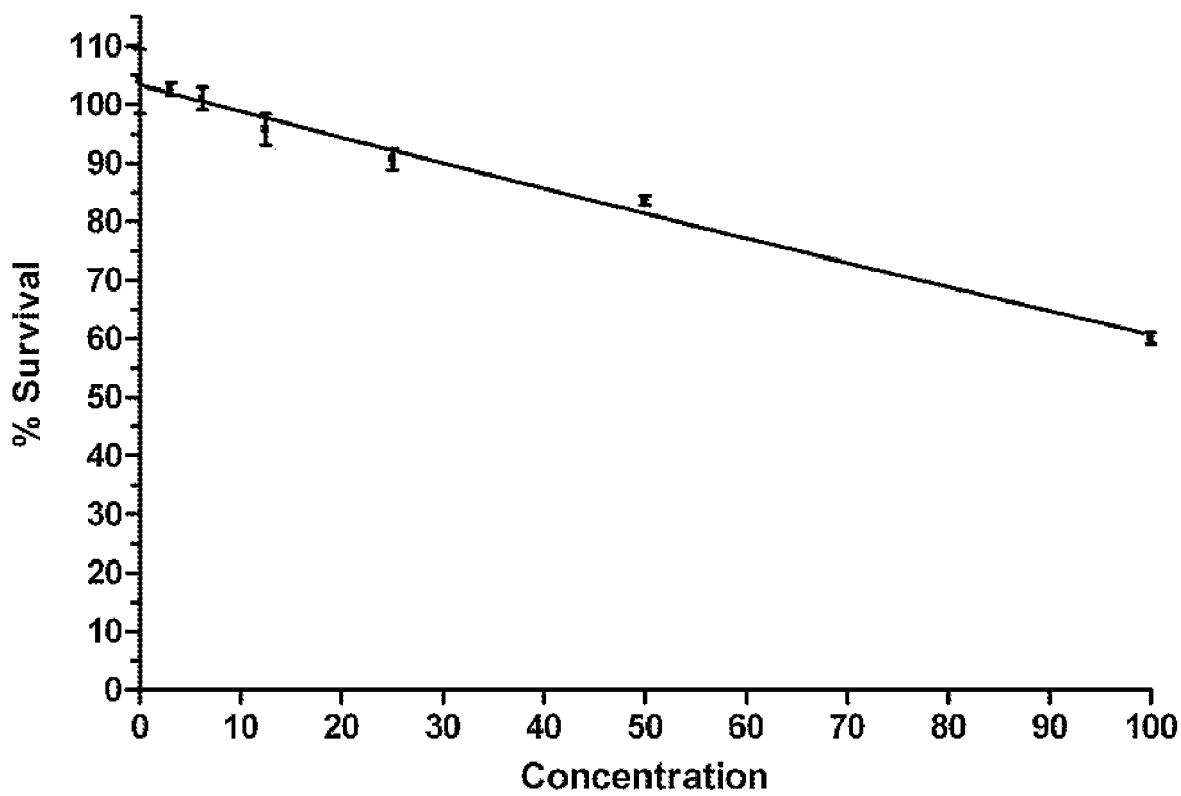
FIG. 10 depicts the low cytotoxicity of SNAFR-6 up to 100 μM.

FIG. 10 depicts the low cytotoxicity we observed for SNAFR-6 up to 100 μM. Compound toxicity was tested by plating 7500 HEp2 cells per well on a Costar 96-well plate. Cells were allowed to grow for 48 hours and were then fed medium containing twofold dilutions of SNAFR-6 ranging from 10 μM to 1.25 μM. Also, 0.1% Saponin (Sigma) was used as a negative control. Cells were then incubated for 24 hours. Viability was measured using the CellTiter Blue Cell Viability assay (Promega) as per manufacturer's instructions. The fluorescence signal was detected using an excitation wavelength of 520 nm and emission wavelength of 584 nm. Viability was normalized against a scale in which untreated cells were rated 100%, and cells treated with 0.1% saponin were rated 0%. At the concentrations tested, the cytotoxicity of SNAFR-6 was low.

Example 42

Photostability of SNAFR-2

FIGS. 9A and 9B depict the photobleaching decay of SNAFR-2 in MeOH, and of fluorescein in 0.1 M NaOH, monitored at the emission maximum of each compound (FIG. 9A), or through a 550 nm long-pass filter (FIG. 9B). The fluorescence intensity was normalized for each compound as compared to the intensity at time t=0. Of the two compounds tested, SNAFR-2 showed considerably higher photostability.

Example 43

Near-Infrared Active Fluorometry Using SNAFR-6

SNAFR-6 possessed the longest wavelength emission in aqueous solution of all of the SNAFRs studied to date. The neutral form of SNAFR-6 could be excited from ~420 nm to ~530 nm. Its emission was centered at 571 nm. The anionic form could be efficiently excited over a broad range from ~420 nm to ~650 nm, with an excitation maximum at 536 nm. The anionic emission ranged from ~575 nm to ~850 nm, centered at 733 nm. SNAFR-6 thus has a very large Stokes shift, 197 nm.

Both the neutral and anionic forms could be excited simultaneously at wavelengths from ~420 nm to ~530 nm, a range that includes both the 488 and 514 nm argon ion laser spectral lines. The neutral emission could be selectively measured by using, for example, an FITC filter set. Also, the anionic form can be selectively excited using a longer excitation wavelength, ~540 nm to ~650 nm. Anionic emission can be selectively measured, using, for example, common Texas Red filter sets. SNAFR-6 is thus a versatile fluorophore for ratiometric measurements. Its p$K_a$ was 8.18±0.03 and 8.10±0.03, as determined by absorption and fluorescence titration experiments, respectively. Significant aggregation in buffered media was not seen.

Figure 7:
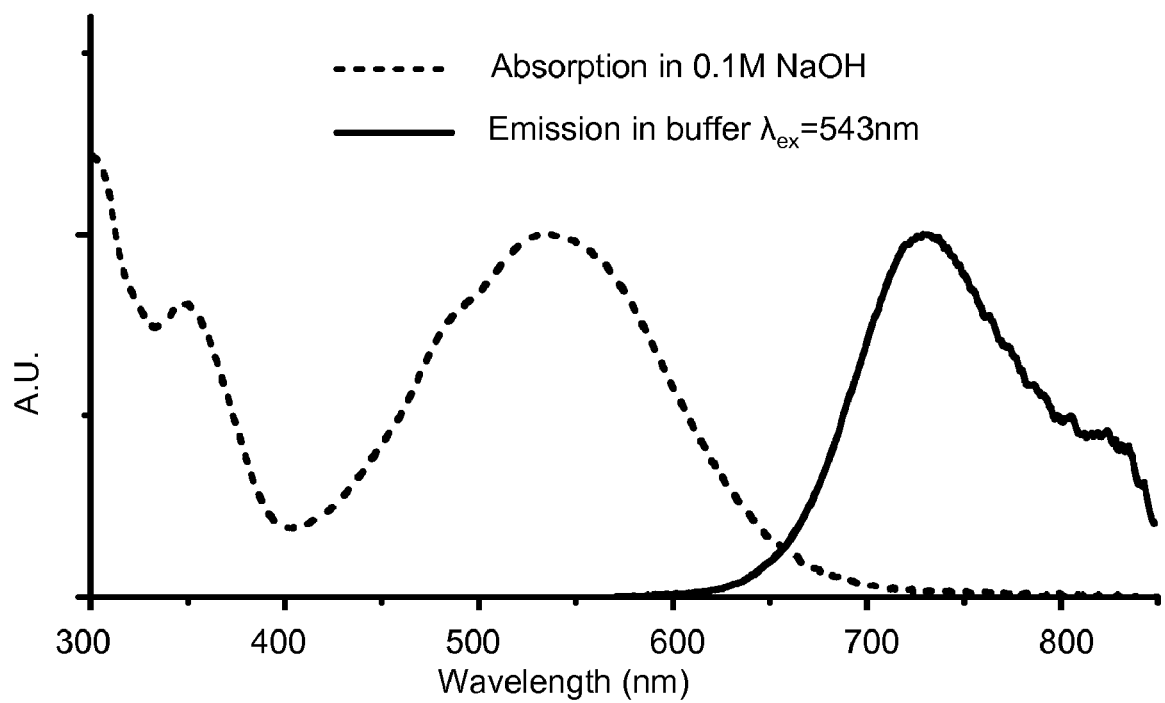
FIG. 7 depicts an overlay of the normalized absorption spectrum of SNAFR-6 in 0.1 M NaOH solution and the NIR emission from its anionic form in phosphate buffer (50 mM, pH 9.3):DMSO 99:1 v/v.

FIG. 7 depicts an overlay of the normalized absorption spectrum of SNAFR-6 in 0.1 M NaOH solution, and the NIR emission from its anionic form in phosphate buffer (50 mM, pH 9.3):DMSO 99:1 v/v. The anionic emission at 733 nm was readily excited throughout a ~200 nm window, a range that includes the common argon ion laser wavelengths of 488 nm and 514 nm. The absorption maximum is located at 536 nm.

SNAFR-6 can be excited using common argon ion lasers, and it emits at near infrared wavelengths, properties that make it particularly attractive for multiplexing. Desirable properties for a fluorophore used in multiplexing are that it should absorb at a common excitation wavelength (typically a that of a common laser); but it should have a distinct emission wavelength or wavelengths, with a large Stokes shift. A current technical challenge is the lack of NIR-emitting dyes with a sufficiently large Stokes shift to accommodate simultaneous excitation with other, commonly-used fluorophores such as fluorescein, rhodamine, coumarin, and BODIPY dyes. SNAFR-6 overcomes these limitations: It is readily excited with an argon ion laser; it emits in the near infrared; it has a large Stokes shift; and it has good photostability.

Cellular imaging studies with HEp2 cells (discussed above) showed that SNAFR-6 readily enters cells, with low cytotoxicity. Co-staining with BODIPY Ceramide, LysoSensor Green, MitoTracker Green, and ERTracker Green showed that most of the compound's signal co-localized with the endoplasmic reticulum (ER), with some punctate signal associated with the lysosomes, possibly partitioning into the membranes.

SNAFR-6 displayed good photostability. Irradiation of an aqueous solution of SNAFR-6 with a Fluorolog®-22Tau3 fluorometer with a 450 W arc lamp, with the instrument's maximum intensity at the compound's absorption maximum did not lead to significant fluorescence bleaching after 1 hour (<2%). By contrast, a fluorescein solution subjected to the same conditions showed 30% bleaching. The quantum yield of the anionic (NIR) emission of SNAFR-6 in DMSO was 0.09, measured by reference to rhodamine 6G in EtOH. This is a relatively high value for an NIR dye emitting at a wavelength longer than ~730 nm.

The complete disclosures of all references cited in this specification are hereby incorporated by reference. Also incorporated by reference are the complete disclosures of the priority application, U.S. provisional patent application 60/832,413; and of each of the following papers, which are believed not to be prior art to the present application: Y. Yang et al., "A convenient preparation of xanthene dyes," *J. Org. Chem.*, vol. 70, pp. 6907-6912 (2005); Y. Yang et al., "An organic white light-emitting fluorophore," *J. Am. Chem. Soc.*, vol. 128, pp. 14081-14092 (2006), including supplemental information available on the web, and with a correction, vol. 129, p. 1008 (2007), Y. Yang, "A near-infrared emission xanthene exhibiting a substantial Stokes shift," including supplemental information available on the web (submitted to *J. Am. Chem. Soc.,* 2007). In the event of an otherwise irreconcilable conflict, the present specification shall take precedence.

We claim:

1. A compound having a structure selected from the group consisting of:

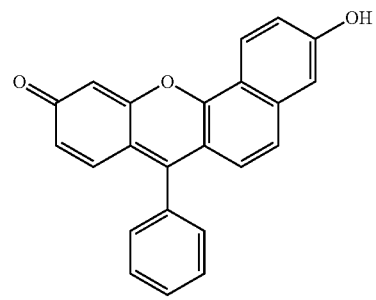

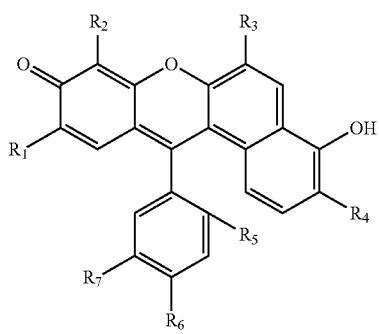

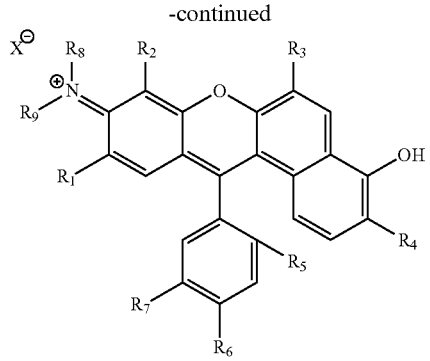

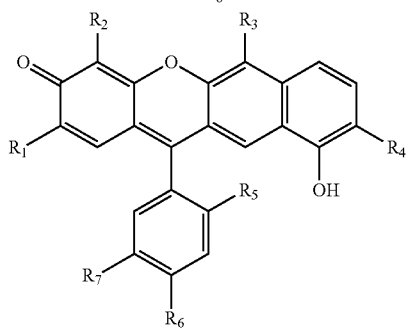

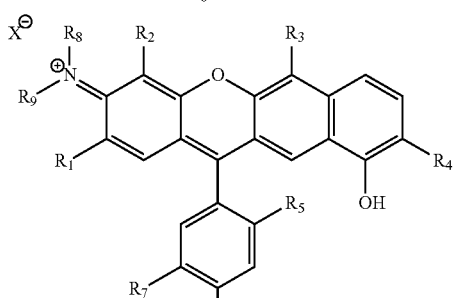

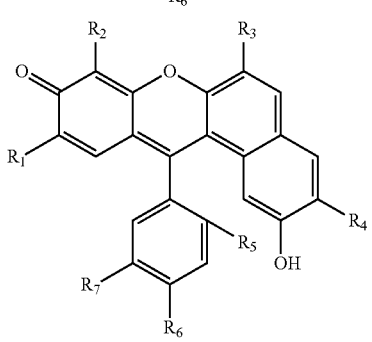

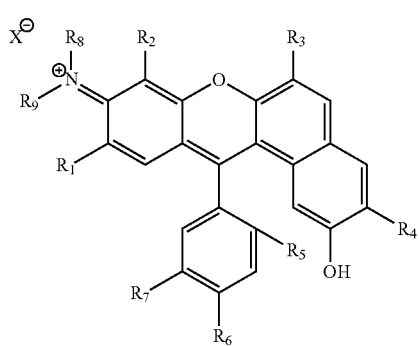

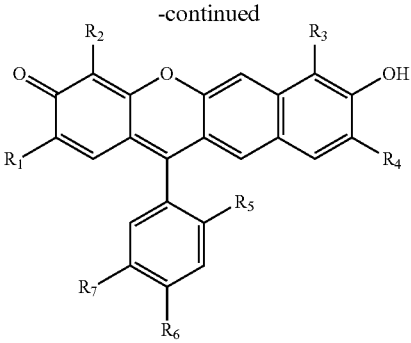

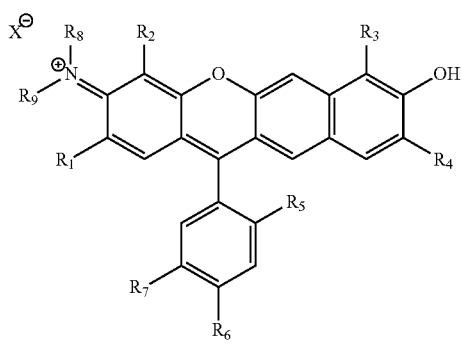

wherein:

R1, R2, R3, R4, R6, and R7 are each independently selected from the group consisting of H, $C_1$ to $C_4$ substituted or unsubstituted alkyl, $C_6$ to $C_{10}$ aryl, $C_1$ to $C_4$ alkenyl, $C_1$ to $C_4$ alkynyl, substituted or unsubstituted amino, halide, hydroxyl, $C_1$ to $C_4$ alkoxy, thio, nitro, $C_1$ to $C_4$ aldehyde, acetyl, $C_1$ to $C_4$ carboxyl, $C_1$ to $C_4$ alkoxycarbonyl, and $C_1$ to $C_4$ alkylaminocarbonyl;

R5 is selected from the group consisting of H, $C_1$ to $C_4$ alkyl, $C_1$ to $C_4$ carboxyl, $C_1$ to $C_4$ alkoxycarbonyl, and $C_1$ to $C_4$ alkylaminocarbonyl;

R8 and R9 are each independently selected from the group consisting of H, and $C_1$ to $C_4$ alkyl; and X is selected from the group consisting of F, Cl, Br, I, $CF_3COO$, and $PF_6$.

2. A compound as recited in claim 1, wherein said compound is selected from the group consisting of

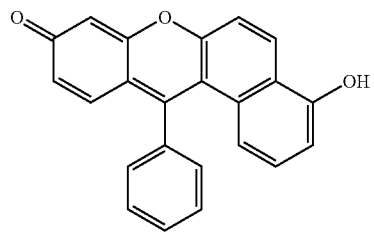

SNAFR-1

SNAFR-2

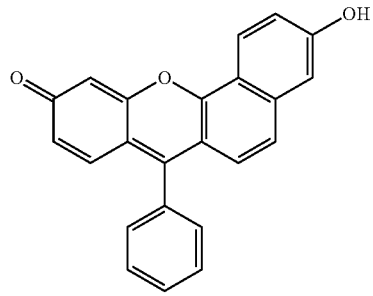

SNAFR-3

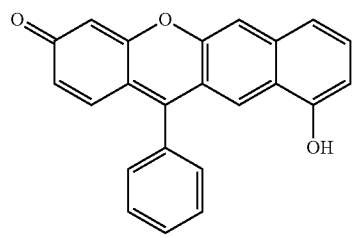

SNAFR-4

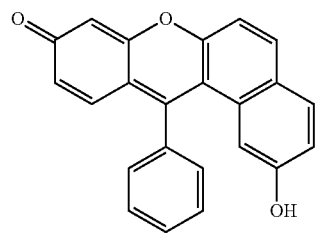

SNAFR-6

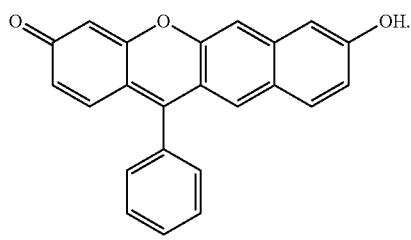

3. A compound as recited in claim 2, wherein said compound is SNAFR-1.

4. A compound as recited in claim 2, wherein said compound is SNAFR-3.

5. A compound as recited in claim 2, wherein said compound is SNAFR-4.

6. A compound as recited in claim 2, wherein said compound is SNAFR-6.

7. A compound as recited in claim 2, wherein said compound is SNAFR-2.

8. A process comprising irradiating with ultraviolet light a solution of the compound SNAFR-2, as recited in claim 7; and allowing the SNAFR-2 to emit light in three distinct regions: one such region having a maximum emission at a wavelength of about 390 nm, one such region having a maximum emission at a wavelength of about 540 nm, and one such region having a maximum emission at a wavelength of about 620 nm; so that the combined emissions are perceived by most humans having normal eyesight as being white light or as being nearly white light.

9. A process comprising irradiating with ultraviolet light a solution of a compound as recited in claim 1; and allowing the compound to emit light in three distinct regions: one such region having a maximum emission at a violet or blue wavelength, one such region having a maximum emission at a green wavelength, and one such region having a maximum emission at a red or orange wavelength; so that the combined emissions are perceived by most humans having normal eyesight as being white light or as being nearly white light.

* * * * *